US007491399B2

(12) United States Patent
Vakharia

(10) Patent No.: US 7,491,399 B2
(45) Date of Patent: *Feb. 17, 2009

(54) IN OVO VACCINE AGAINST INFECTIOUS BURSAL DISEASE

(75) Inventor: Vikram Vakharia, Bowie, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/473,735

(22) Filed: Jun. 23, 2006

(65) Prior Publication Data

US 2006/0292176 A1    Dec. 28, 2006

Related U.S. Application Data

(60) Provisional application No. 60/693,505, filed on Jun. 23, 2005.

(51) Int. Cl.
*A61K 39/12*     (2006.01)
*C12N 7/01*      (2006.01)
*C12N 7/04*      (2006.01)

(52) U.S. Cl. .............. 424/199.1; 424/204.1; 435/235.1; 435/236

(58) Field of Classification Search ................ 435/5, 435/6, 69.1; 424/204.1, 186.1, 199.1, 233.1, 424/205.1, 192.1

See application file for complete search history.

(56) References Cited

U.S. PATENT DOCUMENTS

| | | | | |
|---|---|---|---|---|
| 6,231,868 | B1* | 5/2001 | Vakharia et al. | 424/204.1 |
| 6,451,321 | B1 | 9/2002 | Mundt et al. | |
| 6,485,940 | B2 | 11/2002 | Mundt et al. | |
| 7,022,327 | B1* | 4/2006 | Lutticken et al. | 424/204.1 |
| 2005/0176128 | A1* | 8/2005 | Thies | 435/235.1 |
| 2006/0251663 | A1* | 11/2006 | Mariscal-Gonzalez et al. | 424/159.1 |

FOREIGN PATENT DOCUMENTS

WO          9526196         10/1995

OTHER PUBLICATIONS

Mundt et al., "Vp5 of Infectious Bursal Disease Virus is not Essential for Viral Replication in Cell Culture," Journal of Virology, vol. 71, No. 7 (1997), pp. 5647-5651.*
Yao et al., "Generation of a Mutant Infectious Bursal Disease Virus That Does Not Cause Burdal Lesions," Journal of Virology, vol. 72, No. 4 (1998), pp. 2647-2654.*
Rautenschlein et al. Differences in the immunopathogenesis of infectious bursal disease virus (IBDV) following in ovo and post-hatch vaccination of chickens. Veterinary Immunology and Immunopathology 106 (2005) 139-150.*
Giambrone et al (Avian Diseases 45:144-148, 2001).*
Coletti et al (Avian Diseases 45:1036-1043, 2001).*
Azad, A. A., et al., "The characterization and molecular cloning of the double-stranded RNA genome of an Australian strain of infectious...", "Virology", 1985, pp. 35-44, vol. 143.
Dobos, Peter, "Peptide map comparison of the proteins of infectious bursal disease virus", "Journal of Virology", Dec. 1979, pp. 1046-1050, vol. 32, No. 3.
Giambrone, J. J. et al., "Safety and efficacy of in ovo administration of infectious bursal disease viral vaccines", "Avian Diseases", 2001, pp. 144-148, vol. 45.
Hudson, Peter J., et al., "Genomic structure of the large RNA segment of infectious bursal disease virus", "Nucleic Acids Research", 1986, pp. 5001-5012, vol. 14, No. 12.
Kibenge, F. S. B., et al., "Biochemistry and immunology of infectious bursal disease virus", "J. Gen. Virol.", 1988, pp. 1757-1775, vol. 69.
Lutticken, D., et al., "Determination of the breakthrough titre of IBD vaccines or IBD challenge strains in MDA chickens", "Proceedings of the International Symposium on Infectious Bursal Disease and Chicken Infectiuos Anaemia", 1994, pp. 224-279, Published in: Rauischholzhausen, Germany.
Masteller, Emma L., et al., "B cell development in the chicken", "Poultry Science", 1994, pp. 998-1011, vol. 73.
Mundt, Egbert, et al., "Synthetic transcripts of double-stranded Birnavirus genome are infectious", "Proc. Natl. Acad. Sci. USA", Oct. 1, 1996, pp. 11131-11136, vol. 93, No. 20.
Mundt, Egbert, et al., "Development of a vaccine for immunization against classical as well as variant strains of infectious bursal disease...", "Vaccine", 2003, pp. 4616-4624, vol. 21.
Nunoya, T., et al., "Occurrence of acute infectious bursal disease with high mortality in Japan and Pathogenicity of field isolates in ...", "Avian Diseases", 1992, pp. 597-609, vol. 36.
Sharma, J. M., "Embryo vaccination of chickens with turkey herpesvirus: characteristics of the target cell of early viral replication...", "Avian Pathology", 1987, pp.567-579, vol.16.
Snyder, D. B., et al., "Naturally occuring-neutralizing monoclonal antibody escape variants define the epidemiology of infectious bursal...", "Arch. Virol,", 1992, pp. 89-101, vol. 127.
Snyder, D. B., et al., "Active cross-protection induced by a recombinant baculovirus expressing chimeric infectious bursal disease virus...", "Avian Diseases", 1994, pp. 701-707, vol. 38.
Vakharia, Vikram N., et al., "Molecular basis of antigenic variation in infectious bursal disease virus", "Virus Res.", Feb. 1994, pp. 265-273, vol 31, No. 2.
Vakharia, Vikram N., "Development of recombinant vaccines against infectious bursal disease", "Biotechnology Annual Review", 1997, pp. 151-168, vol. 3.
Van Den Berg, T. P., et al., "Acute infectious bursal disease in poultry: isolation and characterization of highly virulent strain", "Avian Pathology", 1991, pp. 133-143, vol. 20.
Liu, Meihong, "Pathogenesis and Apoptosis Study of Infectious Bursal Disease Virus (IBDV) and Development of a Bivalent Recombinant IBD", Phd Dissertation of Meihong Liu, 2003, Publisher: University of Maryland pp. 67-145 only,

* cited by examiner

*Primary Examiner*—Mary E Mosher
(74) *Attorney, Agent, or Firm*—Steven J. Hultquist; Kelly K. Reynolds; Intellectual Property Technology Law

(57) ABSTRACT

The present invention relates to a non pathogenic vaccine comprising a recombinant Infectious Bursal Disease virus that includes a recombinant Segment A, designated as rD78GLSNSΔ, that includes sequences from D78 and GLS strains and wherein the NS protein is not expressed.

9 Claims, 8 Drawing Sheets

Segment B; Strain D78

SEQ ID NO: 1

MSDIFNSPQARSTISAAFGIKPTAGQDVEELLIPKVWVPPEDPLASPSRLAKFLRENGYKVLQPRSLP
ENEEYETDQILPDLAWMRQIEGAVLKPTLSLPIGDQEYFPKYYPTHRPSKEKPNAYPPDIALLKQMIY
LFLQVPEANEGLKDEVTLLTQNIRDKAYGSGTYMGQATRLVAMKEVATGRNPNKDPLKLGYTFESIA
QLLDITLPVGPPGEDDKPWVPLTRVPSRMLVLTGDVDGDFEVEDYLPKINLKSSSGLPYVGRTKGET
IGEMIAISNQFLRELSTLLKQGAGTKGSNKKKLLSMLSDYWYLSCGLLFPKAERYDKSTWLTKTRNIW
SAPSPTHLMISMITWPVMSNSPNNVLNIEGCPSLYKFNPFRGGLNRIVEWILAPEPKALVYADNIYIVH
SNTWYSIDLEKGEANCTRQHMQAAMYYILTRGWSDNGDPMFNQTWATFAMNIAPALVVDSSCLIM
NLQIKTYGQGSGNAATFINNHLLSTLVLDQWNLMRQPRPDSEEFKSIEDKLGINFKIERSIDDIRGKLR
QLVLLAQPGYLSGGVEPEQSSPTVELDLLGWSATYSKDLGIYVPVLDKERLFCSAAYPKGVENKSLK
SKVGIEQAYKVVRYELRLVGGWNYPLLNKACKNNAGAARRHLEAKGFPLDEFLAEWSELSEFGEAF
EGFNIKLTVTSESLAELNKPVPPKPPNVNRPVNTGGLKAVSNALKTGRYRNEAGLSGLVLLATARSR
LQDAVKAKAEAEKLHKSKPDDPDADWFERSETLSDLLEKADIASKVAHSALVETSDALEAVQSTSVY
TPKYPEVKNPQTASNPVVGLHLPAKRATGVQAALLGAGTSRPMGMEAPTRSKNAVKMAKRRQRQ
KESRORIGIN

SEQ ID NO: 2

1 cctctgggag tcacgaatta acgtggctac taggggcgat acccgccgct ggccgccacg
61 ttagtggctc ctcttcttga tgattctgcc accatgagtg acattttcaa cagtccacag
121 gcgcgaagca cgatctcagc agcgttcggc ataaagccta ctgctggaca agacgtggaa
181 gaactcttga tccctaaagt ttgggtgcca cctgaggatc cgcttgccag ccctagtcga
241 ctggcaaagt tcctcagaga gaacggctac aaagttttgc agccgcggtc tctgcccgag
301 aatgaggagt atgagaccga ccaaatactc ccagacttag catggatgcg acagatagaa
361 ggggctgttt taaaacccac tctatctctc ctattggag atcaggagta cttcccaaag
421 tactacccaa cacatcgccc tagcaaggag aagcccaatg cgtacccgcc agacatcgca
481 ctactcaagc agatgattta cctgtttctc caggttccag aggccaacga gggcctaaag
541 gatgaagtaa ccctcttgac ccaaaacata agggacaagg cctatggaag tgggacctac
601 atgggacaag caactcgact tgtggccatg aaggaggtcg ccactggaag aaacccaaac
661 aaggatcctc taaagcttgg gtacactttt gagagcatcg cgcagctact tgacatcaca
721 ctaccggtag gcccacccgg tgaggatgac aagccctggg tgccactcac aagagtgccg
781 tcacggatgt tggtgctgac gggagacgta gatggcgact tgaggttga agattacctt
841 cccaaaatca acctcaagtc atcaagtgga ctaccatatg taggtcgcac caaggagag
901 acaattggcg agatgatagc tatatcaaac cagtttctca gagagctatc aacactgttg

FIG. 4
(2/4)

```
 961 aagcaaggtg cagggacaaa ggggtcaaac aagaagaagc tactcagcat gttaagtgac
1021 tattggtact tatcatgcgg gcttttgttt ccaaaggctg aaaggtacga caaaagtaca
1081 tggctcacca agacccggaa catatggtca gctccatccc caacacacct catgatctcc
1141 atgatcacct ggcccgtgat gtccaacagc ccaaataacg tgttgaacat tgaagggtgt
1201 ccatcactct acaaattcaa cccgttcaga ggagggttga acaggatcgt cgagtggata
1261 ttggccccgg aagaacccaa ggctcttgta tatgcggaca acatatacat tgtccactca
1321 aacacgtggt actcaattga cctagagaag ggtgaggcaa actgcactcg ccaacacatg
1381 caagccgcaa tgtactacat actcaccaga gggtggtcag acaacggcga cccaatgttc
1441 aatcaaacat gggccaccct tgccatgaac attgcccctg ctctagtggt ggactcatcg
1501 tgcctgataa tgaacctgca aattaagacc tatggtcaag gcagcgggaa tgcagccacg
1561 ttcatcaaca accacctctt gagcacgcta gtgcttgacc agtggaactt gatgagacag
1621 cccagaccag acagcgagga gttcaaatca attgaggaca gctaggtat caactttaag
1681 attgagaggt ccattgatga tatcaggggc aagctgagac agcttgtcct ccttgcacaa
1741 ccagggtacc tgagtggggg ggttgaacca gaacaatcca gcccaactgt tgagcttgac
1801 ctactagggt ggtcagctac atacagcaaa gatctcggga tctatgtgcc ggtgcttgac
1861 aaggaacgcc tattttgttc tgctgcgtat cccaagggag tagagaacaa gagtctcaag
1921 tccaaagtcg ggatcgagca ggcatacaag gtagtcaggt atgaggcgtt gaggttggta
1981 ggtggttgga actacccact cctgaacaaa gcctgcaaga ataacgcagg cgccgctcgg
2041 cggcatctgg aggccaaggg gttcccactc gacgagttcc tagccgagtg gtctgagctg
2101 tcagagttcg gtgaggcctt cgaaggcttc aatatcaagc tgaccgtaac atctgagagc
2161 ctagccgaac tgaacaagcc agtaccccc aagcccccaa atgtcaacag accagtcaac
2221 actgggggac tcaaggcagt cagcaacgcc ctcaagaccg gtcggtacag gaacgaagcc
2281 ggactgagtg gtctcgtcct tctagccaca gcaagaagcc gtctgcaaga tgcagttaag
2341 gccaaggcag aagccgagaa actccacaag tccaagccag acgaccccga tgcagactgg
2401 ttcgaaagat cagaaactct gtcagacctt ctggagaaag ccgacatcgc cagcaaggtc
2461 gcccactcag cactcgtgga acaagcgac gcccttgaag cagttcagtc gacttccgtg
2521 tacacccca agtacccaga agtcaagaac ccacagaccg cctccaaccc cgttgttggg
2581 ctccacctgc ccgccaagag agccaccggt gtccaggccg ctcttctcgg agcaggaacg
2641 agcagaccaa tggggatgga ggccccaaca cggtccaaga acgccgtgaa aatggccaaa
2701 cggcggcaac gccaaaagga gagccgctaa cagccatgat ggga
```

FIG. 4
(3/4)

Segment B VP 1 GLS strain
SEQ ID NO: 3

MSDIFNSPQARSKISAAFGIKPTAGQDVEELLIPKVWVPPEDPLASPSRLAKFLRENGYKVLQPRSLP
ENEEYETDQILPDLAWMRQIEGAVLKPTLSLPIGDQEYFPKYYPTHRPSKEKPNAYPPDIALLKQMIY
LFLQVPEANEGPKDEVTLLTQNIRDKAYGSGTYMGQATRLVAMKEVATGRNPNKDPLKLGYTFESIA
QLLDITLPVGPPGEDDKPWVPLTRVPSRMLVLTGDVDGDFEVEDYLPKINLKSSSGLPYVGRTKGET
IGEMIAISNQFLRELSTLLKQGAGTKGSNKKKLLSMLSDYWYLSCGLLFPKAERYDKSTWLTKTRNIW
SAPSPTHLMISMITWPVMSNSPNNVLNIEGCPSLYKFNPFRGGLNRIVEWILAPEEPKALVYADNIYIV
HSNTWYSIDLEKGEANCTRQHMQAAMYYILTRGWSDNGDPMFNQTWATFAMNIAPALVVDSSCLI
MNLQIKTYGQGSGNAATFINNHLLSTLVLDQWNLMRQPRPDSEEFKSIEDKLGINFKIERSIDDIRGKL
RQLVPLAQPGYLSGGVEPEQSSPTVELDLLGWSATYSKDLGIYVPVLDKERLFCSAAYPKGVENKS
LKSKVGIEQAYKVVRYEALRLVGGWNYPLLNKACKNNAGAARRHLEAKGFPLDEFLAEWSELSEFG
EAFEGFNIKLTVTSESLAELNKPVPPKPPNVNRPVNTGGLKAVSNALKTGRYRNEAGLSGLVLLATA
RSRLQDAVKAKAEAEKLHRSKPDDPDADWFERSETLSDLLEKADIASKVAHSALVETSDALEAVQST
SVYTPKYPEVKNPQTASNPVVGLHLPAKRATGVQAALLGAGTSRPMGMEAPTRSKNAVKMAKRRQ
RQKESRQ

SEQ ID NO: 4

1 ggatacgatg ggtctgaccc tctgggagtc acgaattaac gtggccacta ggggcgatac
61 ccgccgctag ctgccacgtt agtggctcct cttcttgatg attctgccac catgagtgac
121 atattcaaca gtccacaggc gcgaagcaag atctcagcag cgttcggtat aaagcctact
181 gctggacaag acgtggaaga actcttgatc cctaaagttt gggtgccacc tgaggatccg
241 cttgccagcc ctagtcgact ggcaaagttc tcagagaga acggctacaa ggttttgcag
301 ccacggtctc tgcccgagaa tgaggagtat gagaccgacc aaatactccc agacttagca
361 tggatgcgac agatagaagg ggctgtttta aaacctactc tatctctccc cattggagac
421 caggagtact tcccaaagta ctacccaaca catcgcccca gcaaggagaa gcccaatgcg
481 tacccgccag acatcgcact actcaagcag atgatctacc tgtttctcca ggttccagag
541 gccaacgagg gcccaaagga tgaagtgacc ctcctgaccc aaatataag ggataaggcc
601 tatggaagtg ggacctacat gggacaagca actcgacttg tggccatgaa ggaggttgcc
661 actgggagaa acccaaacaa ggatcctcta aaacttgggt acactttga gagcatcgcg
721 cagctgcttg acatcacact accggtaggc ccaccggtg aggatgacaa gccctgggtg
781 ccactcacaa gagtgccatc acgatgttg gtgctgacgg agacgtaga tggcgacttt
841 gaggttgagg attaccttcc caaaatcaac ctcaagtcat caagtggact accgtatgta

FIG. 4
(4/4)

```
 901 ggtcgcacca aaggagagac aattggtgag atgatagcta tctcaaacca gtttctcagg
 961 gagctatcaa cactgttgaa gcaaggtgca gggacaaagg ggtcaaacaa gaagaagcta
1021 ctcagcatgt taagtgacta ttggtactta tcatgcgggc ttttgtttcc aaaggctgaa
1081 aggtacgaca aaagcacatg gctcaccaag acccggaaca tatggtcagc tccatcccca
1141 acacacctca tgatctccat gatcacctgg cccgtgatgt ccaacagccc aataacgtg
1201 ttgaacattg aagggtgtcc atcactctac aaattcaacc cgttcagggg agggttgaac
1261 aggatcgtcg agtggatatt ggctccggaa gaacccaagg cccttgtata tgctgacaac
1321 atatacattg tccactcaaa cacgtggtac tcaattgacc tagagaaggg cgaggcaaac
1381 tgcactcgcc aacacatgca agccgcaatg tactacatcc tcactagagg gtggtccgac
1441 aacggcgacc caatgttcaa tcaaacatgg gccacctttg ccatgaacat tgcccccgct
1501 ctagtggtgg actcatcgtg tctgataatg aatctgcaaa ttaagaccta tggtcaaggc
1561 agcgggaatg cagccacgtt catcaacaac cacctcttga gcacgctagt gcttgaccag
1621 tggaacctga tgagacagcc cagaccagac agcgaggagt tcaaatcaat tgaggacaag
1681 ctaggtatca acttcaagat tgagaggtcc attgatgaca tcaggggcaa gctgagacag
1741 cttgtccccc ttgcacaacc agggtacctg agtggggggg ttgaaccaga acaatccagc
1801 ccaactgttg agcttgacct actagggtgg tcagctacat acagcaaaga tctcgggatc
1861 tatgtgccgg tgcttgacaa ggaacgccta ttttgttctg ctgcgtatcc caagggagtg
1921 gagaacaaga gtctcaagtc taaagtcggg atcgagcagg catacaaggt agtcaggtat
1981 gaggcgttga ggttggtagg tggttggaac tacccactcc tgaacaaagc ctgcaaaaat
2041 aacgcaggcg ccgctcggcg gcatctggag gccaaggggt ttccactcga tgagttccta
2101 gccgagtggt ccgagctgtc agagttcggt gaggccttcg aaggcttcaa tatcaagctg
2161 actgtaacat ccgagagcct agccgaactg aacaagccag tgccccccaa gcccccaaat
2221 gtcaacagac cagtcaacac tggggggactc aaggcagtca gcaacgccct caagaccggt
2281 cgatacagga acgaagccgg actgagtggt ctcgtccttc tagccacagc aagaagccgt
2341 ctgcaagacg cagttaaggc caaggcagaa gccgagaaac tccacaggtc caagcctgac
2401 gaccccgatg cagactggtt tgaaagatca gaaactctgt cagaccttct ggagaaagcc
2461 gacatcgcca gcaaggtcgc ccactcagca ctcgtggaaa caagcgacgc tcttgaagca
2521 gttcagtcga cttccgtgta cacccccaag tacccagaag tcaagaaccc acagaccgcc
2581 tccaaccccg ttgttgggct ccacctgccc gccaagagag ccaccggtgt ccaggccgct
2641 cttctcggag caggaacgag cagaccaatg gggatggagg ccccaacacg gtccaagaac
2701 gccgtgaaaa tggccaaacg gcggcaacgc caaaagaga gccgccaata gccatgatgg
2761 gaaccactca agaagaggac actaatccca gaccccgtat ccccggcctt cgcctgcggg
2821 ggccccc
```

SEQ ID NO: 5

```
ID   D78GLSNS        PRELIMINARY;    DNA;   3261 BP.
DE   D78
CC   NOTE: ORIGINAL SEQUENCE NAME WAS GLSDNA
SQ   SEQUENCE   3261 BP;    873 A;    906 C;    844 G;    638 T; 0 OTHER;
     GGATACGATC GGTCTGACCC CGGGGGAGTC ACCCGGGGAC AGGCCGTCAA GGCCTTGTTC
     CAGGATGGGA CTCCTCCTTC TACAACGCTA TCATTGTAGG TTAGTAGAGA TCAGACAAAC
     GATCGCAGCG ATGACAAACC TGCAAGATCA AACCCAACAG ATTGTTCCGT TCATACGGAG
     CCTTCTGATG CCAACAACCG GACCGGCGTC CATTCCGGAC GACACCCTGG AGAAGCACAC
     TCTCAGGTCA GAGACCTCGA CCTACAATTT GACTGTGGGG ACACAGGGT CAGGGCTAAT
     TGTCTTTTTC CCTGGATTCC CTGGCTCAAT TGTGGGTGCT CACTACACAC TGCAGAGCAA
     TGGGAACTAC AAGTTCGATC AGATGCTCCT GACTGCCCAG AACCTACCGG CCAGCTACAA
     CTACTGCAGG CTAGTGAGTC GGAGTCTCAC AGTAAGGTCA AGCACACTCC CTGGTGGCGT
     TTATGCACTA AACGGCACCA TAAACGCCGT GACCTTCCAA GGAAGCCTGA GTGAACTGAC
     AGATGTTAGC TACAATGGGT TGATGTCTGC AACAGCCAAC ATCAACGACA AAATTGGGAA
     CGTCCTAGTA GGGGAAGGGG TTACTGTCCT CAGCTTACCC ACATCATATG ATCTTGGGTA
     TGTGAGGCTT GGTGACCCCA TTCCCGCAAT AGGGCTTGAC CCAAAAATGG TAGCCACATG
     TGACAGCAGT GACAGGCCCA GAGTCTACAC CATAACTGCA GCCGATGATT ACCAATTCTC
     ATCACAGTAC CAACCAGGTG GGGTAACAAT CACACTGTTC TCAGCCAACA TTGATGCCAT
     CACAAGCCTC AGCGTTGGGG GAGAGCTCGT GTTTCAAACA AGCGTCCACG GCCTTGTACT
     GGGCGCCACC ATCTACCTTA TAGGCTTTGA TGGGTCTGCG GTAATCACTA GAGCTGTGGC
     CGCAAACAAT GGGCTGACGA CCGGCACCGA CAATCTTATG CCATTCAATC TTGTGATTCC
     AACCAACGAG ATAACCCAGC CAATCACATC CATCAAACTG GAGATAGTGA CCTCCAAAAG
     TGGTGGTCAG GAAGGGGACC AGATGTCATG GTCGGCAAGT GGGAGCCTAG CAGTGACGAT
     TCATGGTGGC AACTATCCAG GGGCCCTCCG TCCCGTCACA CTAGTGGCCT ACGAAAGAGT
     GGCAACAGGA TCCGTCGTTA CGGTCGCTGG GGTGAGCAAC TTCGAGCTGA TCCCAAATCC
     TGAACTAGCA AAGAACCTGG TTACAGAATA CGGCCGATTT GACCCAGGAG CCATGAACTA
     CACAAAATTG ATACTGAGTG AGAGGGACCG TCTTGGCATC AAGACCGTCT GGCCAACAAG
     GGAGTACACT GACTTTCGTG AATACTTCAT GGAGGTGGCC GACCTCAACT CTCCCCTGAA
     GATTGCAGGA GCATTCGGCT TCAAAGACAT AATCCGGGCC ATAAGGAGGA TAGCTGTGCC
     GGTGGTCTCC ACATTGTTCC CACCTGCCGC TCCCCTAGCC CATGCAATTG GGGAAGGTGT
     AGACTACCTG CTGGGCGATG AGGCACAGGC TGCTTCAGGA ACTGCTCGAG CCGCGTCAGG
     AAAAGCAAGA GCTGCCTCAG GCCGCATAAG GCAGCTGACT CTCGCCGCCG ACAAGGGGTA
     CGAGGTAGTC GCGAATCTAT TCCAGGTGCC CCAGAATCCC GTAGTCGACG GGATTCTTGC
     TTCACCTGGG GTACTCCGCG GTGCACACAA CCTCGACTGC GTGTTAAGAG AGGGTGCCAC
     GCTATTCCCT GTGGTTATTA CGACAGTGGA AGACGCCATG ACACCCAAAG CATTGAACAG
     CAAAATGTTT GCTGTCATTG AAGGCGTGCG AGAAGACCTC AACCTCCAT CTCAAAGAGG
     ATCCTTCATA CGAACTCTCT CTGGACACAG AGTCTATGGA TATGCTCCAG ATGGGGTACT
     TCCACTGGAG ACTGGGAGAG ACTACACCGT TGTCCCAATA GATGATGTCT GGGACGACAG
     CATTATGCTG TCCAAAGATC CCATACCTCC TATTGTGGGA AACAGTGGAA ATCTAGCCAT
     AGCTTACATG GATGTGTTTC GACCCAAAGT CCCAATCCAT GTGGCTATGA CGGGAGCCCT
     CAATGCTTGT GGCGAGATTG AGAAAGTAAG CTTTAGAAGC ACCAAGCTCG CCACTGCACA
     CCGACTTGGC CTTAGGTTGG CTGGTCCCGG AGCATTCGAT GTAAACACCG GCCCAACTG
     GGCAACGTTC ATCAAACGTT TCCCTCACAA TCCACGCGAC TGGGACAGGC TCCCCTACCT
     CAACCTACCA TACCTTCCAC CCAATGCAGG ACGCCAGTAC CACCTTGCCA TGGCTGCATC
     AGAGTTCAAA GAGACCCCCG AACTCGAGAG TGCCGTCAGA GCAATGGAAG CAGCAGCCAA
     CGTGGACCCA CTATTCCAAT CTGCACTCAG TGTGTTCATG TGGCTGGAAG AGAATGGGAT
     TGTGACTGAC ATGGCCAACT TCGCACTCAG CGACCCGAAC GCCATCGGA TGCGAAATTT
     TCTTGCAAAC GCACCACAAG CAGGCAGCAA GTCGCAAAGG GCCAAGTACG GGACAGCAGG
     CTACGAGTG GAGGCTCGGG GCCCCACACC AGAGGAAGCA CAGAGGGAAA AAGACACACG
     GATCTCAAAG AAGATGGAGA CCATGGGCAT CTACTTTGCA ACACCAGAAT GGGTAGCACT
     CAATGGGCAC CGAGGGCCAA GCCCCGGCCA GCTAAAGTAC TGGCAGAACA CACGAGAAAT
     ACCGGACCCA AACGAGGACT ATCTAGACTA CGTGCATGCA GAGAAGAGCC GGTTGGCATC
     AGAAGAACAA ATCCTAAGGG CAGCTACGTC GATCTACGGG CTCCAGGAC AGGCAGAGCC
     ACCCCAAGCT TTCATAGACG AAGTTGCCAA AGTCTATGAA ATCAACCATG ACGTGGCCC
     AAACCAAGAA CAGATGAAAG ATCTGCTCTT GACTGCGATG GAGATGAAGC ATCGCAATCC
     CAGGCGGGCT CTACCAAAGC CCAAGCCAAA ACCCAATGCT CCAACACAGA GACCCCCTGG
     TCGGCTGGGC CGCTGGATCA GGACCGTCTC TGATGAGGAC CTTGAGTGAG GCTCCTGGGA
     GTCTCCCGAC ACCACCCGCG CAGGTGTGGA CACCAATTCG GCCTTACAAC ATCCCAAATT
     GGATCCGTTC GCGGGTCCCC T
```

Figure 5

SEQUENCE LISTING

```
<160> NUMBER OF SEQ ID NOS: 5

<210> SEQ ID NO 1
<211> LENGTH: 876
<212> TYPE: PRT
<213> ORGANISM: Artificial
<220> FEATURE:
<223> OTHER INFORMATION: synthetic construct

<400> SEQUENCE: 1

Met Ser Asp Ile Phe Asn Ser Pro Gln Ala Arg Ser Thr Ile Ser Ala
1               5                   10                  15

Ala Phe Gly Ile Lys Pro Thr Ala Gly Gln Asp Val Glu Glu Leu Leu
                20                  25                  30

Ile Pro Lys Val Trp Val Pro Pro Glu Asp Pro Leu Ala Ser Pro Ser
            35                  40                  45

Arg Leu Ala Lys Phe Leu Arg Glu Asn Gly Tyr Lys Val Leu Gln Pro
    50                  55                  60

Arg Ser Leu Pro Glu Asn Glu Glu Tyr Glu Thr Asp Gln Ile Leu Pro
65                  70                  75                  80

Asp Leu Ala Trp Met Arg Gln Ile Glu Gly Ala Val Leu Lys Pro Thr
                85                  90                  95

Leu Ser Leu Pro Ile Gly Asp Gln Glu Tyr Phe Pro Lys Tyr Tyr Pro
                100                 105                 110

Thr His Arg Pro Ser Lys Glu Lys Pro Asn Ala Tyr Pro Pro Asp Ile
            115                 120                 125

Ala Leu Leu Lys Gln Met Ile Tyr Leu Phe Leu Gln Val Pro Glu Ala
        130                 135                 140

Asn Glu Gly Leu Lys Asp Glu Val Thr Leu Leu Thr Gln Asn Ile Arg
145                 150                 155                 160

Asp Lys Ala Tyr Gly Ser Gly Thr Tyr Met Gly Gln Ala Thr Arg Leu
                165                 170                 175

Val Ala Met Lys Glu Val Ala Thr Gly Arg Asn Pro Asn Lys Asp Pro
                180                 185                 190

Leu Lys Leu Gly Tyr Thr Phe Glu Ser Ile Ala Gln Leu Leu Asp Ile
            195                 200                 205
```

-continued

```
Thr Leu Pro Val Gly Pro Pro Gly Glu Asp Lys Pro Trp Val Pro
    210                 215                 220
Leu Thr Arg Val Pro Ser Arg Met Leu Val Leu Thr Gly Asp Val Asp
225                 230                 235                 240
Gly Asp Phe Glu Val Glu Asp Tyr Leu Pro Lys Ile Asn Leu Lys Ser
                245                 250                 255
Ser Ser Gly Leu Pro Tyr Val Gly Arg Thr Lys Gly Glu Thr Ile Gly
                260                 265                 270
Glu Met Ile Ala Ile Ser Asn Gln Phe Leu Arg Glu Leu Ser Thr Leu
            275                 280                 285
Leu Lys Gln Gly Ala Gly Thr Lys Gly Ser Asn Lys Lys Leu Leu
    290                 295                 300
Ser Met Leu Ser Asp Tyr Trp Tyr Leu Ser Cys Gly Leu Leu Phe Pro
305                 310                 315                 320
Lys Ala Glu Arg Tyr Asp Lys Ser Thr Trp Leu Thr Lys Thr Arg Asn
                325                 330                 335
Ile Trp Ser Ala Pro Ser Pro Thr His Leu Met Ile Ser Met Ile Thr
                340                 345                 350
Trp Pro Val Met Ser Asn Ser Pro Asn Val Leu Asn Ile Glu Gly
            355                 360                 365
Cys Pro Ser Leu Tyr Lys Phe Asn Pro Phe Arg Gly Gly Leu Asn Arg
    370                 375                 380
Ile Val Glu Trp Ile Leu Ala Pro Glu Pro Lys Ala Leu Val Tyr Ala
385                 390                 395                 400
Asp Asn Ile Tyr Ile Val His Ser Asn Thr Trp Tyr Ser Ile Asp Leu
                405                 410                 415
Glu Lys Gly Glu Ala Asn Cys Thr Arg Gln His Met Gln Ala Ala Met
            420                 425                 430
Tyr Tyr Ile Leu Thr Arg Gly Trp Ser Asp Asn Gly Asp Pro Met Phe
    435                 440                 445
Asn Gln Thr Trp Ala Thr Phe Ala Met Asn Ile Ala Pro Ala Leu Val
    450                 455                 460
Val Asp Ser Ser Cys Leu Ile Met Asn Leu Gln Ile Lys Thr Tyr Gly
465                 470                 475                 480
Gln Gly Ser Gly Asn Ala Ala Thr Phe Ile Asn Asn His Leu Leu Ser
                485                 490                 495
Thr Leu Val Leu Asp Gln Trp Asn Leu Met Arg Gln Pro Arg Pro Asp
            500                 505                 510
Ser Glu Glu Phe Lys Ser Ile Glu Asp Lys Leu Gly Ile Asn Phe Lys
    515                 520                 525
Ile Glu Arg Ser Ile Asp Asp Ile Arg Gly Lys Leu Arg Gln Leu Val
    530                 535                 540
Leu Leu Ala Gln Pro Gly Tyr Leu Ser Gly Gly Val Glu Pro Glu Gln
545                 550                 555                 560
Ser Ser Pro Thr Val Glu Leu Asp Leu Leu Gly Trp Ser Ala Thr Tyr
                565                 570                 575
Ser Lys Asp Leu Gly Ile Tyr Val Pro Val Leu Asp Lys Glu Arg Leu
            580                 585                 590
Phe Cys Ser Ala Ala Tyr Pro Lys Gly Val Glu Asn Lys Ser Leu Lys
    595                 600                 605
Ser Lys Val Gly Ile Glu Gln Ala Tyr Lys Val Val Arg Tyr Glu Leu
    610                 615                 620
Arg Leu Val Gly Gly Trp Asn Tyr Pro Leu Leu Asn Lys Ala Cys Lys
```

```
                625                 630                 635                 640
Asn Asn Ala Gly Ala Arg Arg His Leu Glu Ala Lys Gly Phe Pro
                    645                 650                 655
Leu Asp Glu Phe Leu Ala Glu Trp Ser Glu Leu Ser Glu Phe Gly Glu
                660                 665                 670
Ala Phe Glu Gly Phe Asn Ile Lys Leu Thr Val Thr Ser Glu Ser Leu
            675                 680                 685
Ala Glu Leu Asn Lys Pro Val Pro Pro Lys Pro Asn Val Asn Arg
        690                 695                 700
Pro Val Asn Thr Gly Gly Leu Lys Ala Val Ser Asn Ala Leu Lys Thr
705                 710                 715                 720
Gly Arg Tyr Arg Asn Glu Ala Gly Leu Ser Gly Leu Val Leu Leu Ala
                725                 730                 735
Thr Ala Arg Ser Arg Leu Gln Asp Ala Val Lys Ala Lys Ala Glu Ala
                740                 745                 750
Glu Lys Leu His Lys Ser Lys Pro Asp Asp Pro Asp Ala Asp Trp Phe
                755                 760                 765
Glu Arg Ser Glu Thr Leu Ser Asp Leu Leu Lys Ala Asp Ile Ala
770                 775                 780
Ser Lys Val Ala His Ser Ala Leu Val Glu Thr Ser Asp Ala Leu Glu
785                 790                 795                 800
Ala Val Gln Ser Thr Ser Val Tyr Thr Pro Lys Tyr Pro Glu Val Lys
                805                 810                 815
Asn Pro Gln Thr Ala Ser Asn Pro Val Val Gly Leu His Leu Pro Ala
            820                 825                 830
Lys Arg Ala Thr Gly Val Gln Ala Ala Leu Leu Gly Ala Gly Thr Ser
            835                 840                 845
Arg Pro Met Gly Met Glu Ala Pro Thr Arg Ser Lys Asn Ala Val Lys
        850                 855                 860
Met Ala Lys Arg Arg Gln Arg Gln Lys Glu Ser Arg
865                 870                 875

<210> SEQ ID NO 2
<211> LENGTH: 2744
<212> TYPE: DNA
<213> ORGANISM: Artificial
<220> FEATURE:
<223> OTHER INFORMATION: sythetic construct

<400> SEQUENCE: 2
cctctgggag tcacgaatta acgtggctac taggggcgat acccgccgct ggccgccacg     60
ttagtggctc ctcttcttga tgattctgcc accatgagtg acattttcaa cagtccacag    120
gcgcgaagca cgatctcagc agcgttcggc ataaagccta ctgctggaca agacgtggaa    180
gaactcttga tccctaaagt ttgggtgcca cctgaggatc cgcttgccag ccctagtcga    240
ctggcaaagt tcctcagaga aacggctac aaagttttgc agccgcggtc tctgcccgag    300
aatgaggagt atgagaccga ccaaatactc ccagacttag catggatgcg acagatagaa    360
ggggctgttt taaacccac tctatctctc cctattggag atcaggagta cttcccaaag    420
tactacccaa cacatcgccc tagcaaggag aagcccaatg cgtacccgcc agacatcgca    480
ctactcaagc agatgattta cctgtttctc caggttccag aggccaacga gggcctaaag    540
gatgaagtaa ccctcttgac ccaaaacata agggacaagg cctatggaag tgggacctac    600
atgggacaag caactcgact tgtggccatg aaggaggtcg ccactggaag aaacccaaac    660
```

```
aaggatcctc taaagcttgg gtacactttt gagagcatcg cgcagctact tgacatcaca    720
ctaccggtag gcccacccgg tgaggatgac aagccctggg tgccactcac aagagtgccg    780
tcacggatgt tggtgctgac gggagacgta gatggcgact ttgaggttga agattacctt    840
cccaaaatca acctcaagtc atcaagtgga ctaccatatg taggtcgcac caaaggagag    900
acaattggcg agatgatagc tatatcaaac cagtttctca gagagctatc aacactgttg    960
aagcaaggtg cagggacaaa ggggtcaaac aagaagaagc tactcagcat gttaagtgac   1020
tattggtact tatcatgcgg gcttttgttt ccaaaggctg aaaggtacga caaaagtaca   1080
tggctcacca agacccggaa catatggtca gctccatccc caacacacct catgatctcc   1140
atgatcacct ggcccgtgat gtccaacagc ccaataacg tgttgaacat gaagggtgt    1200 ccatcactct acaaattcaa cccgttcaga ggagggttga acaggatcgt cgagtggata   1260
ttggccccgg aagaacccaa ggctcttgta tatgcggaca acatatacat tgtccactca   1320
aacacgtggt actcaattga cctagagaag ggtgaggcaa actgcactcg ccaacacatg   1380
caagccgcaa tgtactacat actcaccaga gggtggtcag acaacggcga cccaatgttc   1440
aatcaaacat gggccacctt tgccatgaac attgccctg ctctagtggt ggactcatcg    1500
tgcctgataa tgaacctgca aattaagacc tatggtcaag cagcgggaa tgcagccacg    1560 ttcatcaaca accacctctt gagcacgcta gtgcttgacc agtggaactt gatgagacag   1620
cccagaccag acagcgagga gttcaaatca attgaggaca agctaggtat caactttaag   1680
attgagaggt ccattgatga tatcaggggc aagctgagac agcttgtcct ccttgcacaa   1740
ccagggtacc tgagtggggg ggttgaacca gaacaatcca gcccaactgt tgagcttgac   1800
ctactagggt ggtcagctac atacagcaaa gatctcggga tctatgtgcc ggtgcttgac   1860
aaggaacgcc tattttgttc tgctgcgtat cccaagggag tagagaacaa gagtctcaag   1920
tccaaagtcg ggatcgagca ggcatacaag gtagtcaggt atgaggcgtt gaggttggta   1980
ggtggttgga actacccact cctgaacaaa gcctgcaaga ataacgcagg cgccgctcgg   2040
cggcatctgg aggccaaggg gttcccactc gacgagttcc tagccgagtg gtctgagctg   2100
tcagagttcg gtgaggcctt cgaaggcttc aatatcaagc tgaccgtaac atctgagagc   2160
ctagccgaac tgaacaagcc agtaccccc aagcccccaa atgtcaacag accagtcaac    2220
actgggggac tcaaggcagt cagcaacgcc ctcaagaccg gtcggtacag gaacgaagcc   2280
ggactgagtg gtctcgtcct tctagccaca gcaagaagcc gtctgcaaga tgcagttaag   2340
gccaaggcag aagccgagaa actccacaag tccaagccag acgaccccga tgcagactgg   2400
ttcgaaagat cagaaactct gtcagacctt ctggagaaag ccgacatcgc cagcaaggtc   2460
gcccactcag cactcgtgga aacaagcgac gcccttgaag cagttcagtc gacttccgtg   2520 tacacccca gtacccagag agtcaagaac ccacagaccg cctccaaccc cgttgttggg    2580
ctccacctgc ccgccaagag agccaccggt gtccaggccc tcttctcgg agcaggaacg    2640 agcagaccaa tggggatgga ggccccaaca cggtccaaga acgccgtgaa aatggccaaa    2700
cggcggcaac gccaaaagga gagccgctaa cagccatgat ggga                    2744
```

<210> SEQ ID NO 3
<211> LENGTH: 879
<212> TYPE: PRT
<213> ORGANISM: Artificial
<220> FEATURE:
<223> OTHER INFORMATION: synthetic construct

<400> SEQUENCE: 3

```
Met Ser Asp Ile Phe Asn Ser Pro Gln Ala Arg Ser Lys Ile Ser Ala
1               5                   10                  15

Ala Phe Gly Ile Lys Pro Thr Ala Gly Gln Asp Val Glu Glu Leu Leu
            20                  25                  30

Ile Pro Lys Val Trp Val Pro Glu Asp Pro Leu Ala Ser Pro Ser
        35                  40                  45

Arg Leu Ala Lys Phe Leu Arg Glu Asn Gly Tyr Lys Val Leu Gln Pro
    50                  55                  60

Arg Ser Leu Pro Glu Asn Glu Glu Tyr Glu Thr Asp Gln Ile Leu Pro
65                  70                  75                  80

Asp Leu Ala Trp Met Arg Gln Ile Glu Gly Ala Val Leu Lys Pro Thr
                85                  90                  95

Leu Ser Leu Pro Ile Gly Asp Gln Glu Tyr Phe Pro Lys Tyr Tyr Pro
                100                 105                 110

Thr His Arg Pro Ser Lys Glu Lys Pro Asn Ala Tyr Pro Pro Asp Ile
            115                 120                 125

Ala Leu Leu Lys Gln Met Ile Tyr Leu Phe Leu Gln Val Pro Glu Ala
130                 135                 140

Asn Glu Gly Pro Lys Asp Glu Val Thr Leu Leu Thr Gln Asn Ile Arg
145                 150                 155                 160

Asp Lys Ala Tyr Gly Ser Gly Thr Tyr Met Gly Gln Ala Thr Arg Leu
                165                 170                 175

Val Ala Met Lys Glu Val Ala Thr Gly Arg Asn Pro Asn Lys Asp Pro
            180                 185                 190

Leu Lys Leu Gly Tyr Thr Phe Glu Ser Ile Ala Gln Leu Leu Asp Ile
        195                 200                 205

Thr Leu Pro Val Gly Pro Pro Gly Glu Asp Lys Pro Trp Val Pro
    210                 215                 220

Leu Thr Arg Val Pro Ser Arg Met Leu Val Leu Thr Gly Asp Val Asp
225                 230                 235                 240

Gly Asp Phe Glu Val Glu Asp Tyr Leu Pro Lys Ile Asn Leu Lys Ser
                245                 250                 255

Ser Ser Gly Leu Pro Tyr Val Gly Arg Thr Lys Gly Glu Thr Ile Gly
            260                 265                 270

Glu Met Ile Ala Ile Ser Asn Gln Phe Leu Arg Glu Leu Ser Thr Leu
            275                 280                 285

Leu Lys Gln Gly Ala Gly Thr Lys Gly Ser Asn Lys Lys Lys Leu Leu
    290                 295                 300

Ser Met Leu Ser Asp Tyr Trp Tyr Leu Ser Cys Gly Leu Leu Phe Pro
305                 310                 315                 320

Lys Ala Glu Arg Tyr Asp Lys Ser Thr Trp Leu Thr Lys Thr Arg Asn
                325                 330                 335

Ile Trp Ser Ala Pro Ser Pro Thr His Leu Met Ile Ser Met Ile Thr
                340                 345                 350

Trp Pro Val Met Ser Asn Ser Pro Asn Asn Val Leu Asn Ile Glu Gly
            355                 360                 365

Cys Pro Ser Leu Tyr Lys Phe Asn Pro Phe Arg Gly Gly Leu Asn Arg
        370                 375                 380

Ile Val Glu Trp Ile Leu Ala Pro Glu Glu Pro Lys Ala Leu Val Tyr
385                 390                 395                 400

Ala Asp Asn Ile Tyr Ile Val His Ser Asn Thr Trp Tyr Ser Ile Asp
                405                 410                 415
```

```
Leu Glu Lys Gly Glu Ala Asn Cys Thr Arg Gln His Met Gln Ala Ala
            420                 425                 430

Met Tyr Tyr Ile Leu Thr Arg Gly Trp Ser Asp Asn Gly Asp Pro Met
            435                 440                 445

Phe Asn Gln Thr Trp Ala Thr Phe Ala Met Asn Ile Ala Pro Ala Leu
            450                 455                 460

Val Val Asp Ser Ser Cys Leu Ile Met Asn Leu Gln Ile Lys Thr Tyr
465                 470                 475                 480

Gly Gln Gly Ser Gly Asn Ala Ala Thr Phe Ile Asn Asn His Leu Leu
                485                 490                 495

Ser Thr Leu Val Leu Asp Gln Trp Asn Leu Met Arg Gln Pro Arg Pro
            500                 505                 510

Asp Ser Glu Glu Phe Lys Ser Ile Glu Asp Lys Leu Gly Ile Asn Phe
            515                 520                 525

Lys Ile Glu Arg Ser Ile Asp Asp Ile Arg Gly Lys Leu Arg Gln Leu
            530                 535                 540

Val Pro Leu Ala Gln Pro Gly Tyr Leu Ser Gly Val Glu Pro Glu
545                 550                 555                 560

Gln Ser Ser Pro Thr Val Glu Leu Asp Leu Leu Gly Trp Ser Ala Thr
                565                 570                 575

Tyr Ser Lys Asp Leu Gly Ile Tyr Val Pro Val Leu Asp Lys Glu Arg
            580                 585                 590

Leu Phe Cys Ser Ala Ala Tyr Pro Lys Gly Val Glu Asn Lys Ser Leu
            595                 600                 605

Lys Ser Lys Val Gly Ile Glu Gln Ala Tyr Lys Val Val Arg Tyr Glu
            610                 615                 620

Ala Leu Arg Leu Val Gly Gly Trp Asn Tyr Pro Leu Leu Asn Lys Ala
625                 630                 635                 640

Cys Lys Asn Asn Ala Gly Ala Ala Arg Arg His Leu Glu Ala Lys Gly
                645                 650                 655

Phe Pro Leu Asp Glu Phe Leu Ala Glu Trp Ser Glu Leu Ser Glu Phe
            660                 665                 670

Gly Glu Ala Phe Glu Gly Phe Asn Ile Lys Leu Thr Val Thr Ser Glu
            675                 680                 685

Ser Leu Ala Glu Leu Asn Lys Pro Val Pro Lys Pro Pro Asn Val
            690                 695                 700

Asn Arg Pro Val Asn Thr Gly Leu Lys Ala Val Ser Asn Ala Leu
705                 710                 715                 720

Lys Thr Gly Arg Tyr Arg Asn Glu Ala Gly Leu Ser Gly Leu Val Leu
                725                 730                 735

Leu Ala Thr Ala Arg Ser Arg Leu Gln Asp Ala Val Lys Ala Lys Ala
            740                 745                 750

Glu Ala Glu Lys Leu His Arg Ser Lys Pro Asp Asp Pro Asp Ala Asp
            755                 760                 765

Trp Phe Glu Arg Ser Glu Thr Leu Ser Asp Leu Leu Glu Lys Ala Asp
            770                 775                 780

Ile Ala Ser Lys Val Ala His Ser Ala Leu Val Glu Thr Ser Asp Ala
785                 790                 795                 800

Leu Glu Ala Val Gln Ser Thr Ser Val Tyr Thr Pro Lys Tyr Pro Glu
                805                 810                 815

Val Lys Asn Pro Gln Thr Ala Ser Asn Pro Val Val Gly Leu His Leu
            820                 825                 830

Pro Ala Lys Arg Ala Thr Gly Val Gln Ala Ala Leu Leu Gly Ala Gly
```

```
                835                 840                 845
Thr Ser Arg Pro Met Gly Met Glu Ala Pro Thr Arg Ser Lys Asn Ala
    850                 855                 860

Val Lys Met Ala Lys Arg Arg Gln Arg Gln Lys Glu Ser Arg Gln
865                 870                 875

<210> SEQ ID NO 4
<211> LENGTH: 2827
<212> TYPE: DNA
<213> ORGANISM: Artificial
<220> FEATURE:
<223> OTHER INFORMATION: synthetic construct

<400> SEQUENCE: 4
ggatacgatg ggtctgaccc tctgggagtc acgaattaac gtggccacta ggggcgatac      60
ccgccgctag ctgccacgtt agtggctcct cttcttgatg attctgccac catgagtgac     120
atattcaaca gtccacaggc gcgaagcaag atctcagcag cgttcggtat aaagcctact     180
gctggacaag acgtggaaga actcttgatc cctaaagttt gggtgccacc tgaggatccg     240
cttgccagcc ctagtcgact ggcaaagttc tcagagaga acggctacaa ggttttgcag      300
ccacggtctc tgcccgagaa tgaggagtat gagaccgacc aaatactccc agacttagca     360
tggatgcgac agatagaagg ggctgtttta aaacctactc tatctctccc cattggagac     420
caggagtact tcccaaagta ctacccaaca catcgcccca gcaaggagaa gcccaatgcg     480
tacccgccag acatcgcact actcaagcag atgatctacc tgtttctcca ggttccagag     540
gccaacgagg gcccaaagga tgaagtgacc ctcctgaccc aaaatataag ggataaggcc     600
tatggaagtg ggacctacat gggacaagca actcgacttg tggccatgaa ggaggttgcc     660
actgggagaa acccaaacaa ggatcctcta aaacttgggt acacttttga gagcatcgcg     720
cagctgcttg acatcacact accggtaggc ccacccggtg aggatgacaa gccctgggtg     780
ccactcacaa gagtgccatc acggatgttg gtgctgacgg gagacgtaga tggcgacttt     840
gaggttgagg attaccttcc caaaatcaac ctcaagtcat caagtggact accgtatgta     900
ggtcgcacca aggagagac aattggtgag atgatagcta tctcaaacca gtttctcagg      960
gagctatcaa cactgttgaa gcaaggtgca gggacaaagg ggtcaaacaa gaagaagcta    1020
ctcagcatgt taagtgacta ttggtactta tcatgcgggc ttttgtttcc aaaggctgaa    1080
aggtacgaca aaagcacatg gctcaccaag acccggaaca tatggtcagc tccatcccca    1140
acacacctca tgatctccat gatcacctgg cccgtgatgt ccaacagccc aaataacgtg    1200
ttgaacattg aagggtgtcc atcactctac aaattcaacc cgttcaggg agggttgaac     1260 aggatcgtcg agtggatatt ggctccggaa gaacccaagg cccttgtata tgctgacaac    1320
atatacattg tccactcaaa cacgtggtac tcaattgacc tagagaaggg cgaggcaaac    1380
tgcactcgcc aacacatgca agccgcaatg tactacatcc tcactagagg gtggtccgac    1440
aacggcgacc caatgttcaa tcaaacatgg gccacctttg ccatgaacat gcccccgct     1500 ctagtggtgg actcatcgtg tctgataatg aatctgcaaa ttaagaccta tggtcaaggc    1560
agcgggaatg cagccacgtt catcaacaac cacctcttga gcacgctagt gcttgaccag    1620
tggaacctga tgagacagcc cagaccgac agcgaggagt caaatcaat tgaggacaag     1680 ctaggtatca acttcaagat tgagaggtcc attgatgaca tcaggggcaa gctgagacag    1740
cttgtccccc ttgcacaacc agggtacctg agtgggggg ttgaaccaga acaatccagc     1800
ccaactgttg agcttgacct actagggtgg tcagctacat acagcaaaga tctcgggatc    1860
```

```
tatgtgccgg tgcttgacaa ggaacgccta ttttgttctg ctgcgtatcc caagggagtg    1920
gagaacaaga gtctcaagtc taaagtcggg atcgagcagg catacaaggt agtcaggtat    1980
gaggcgttga ggttggtagg tggttggaac tacccactcc tgaacaaagc ctgcaaaaat    2040
aacgcaggcg ccgctcggcg gcatctggag gccaaggggt ttccactcga tgagttccta    2100
gccgagtggt ccgagctgtc agagttcggt gaggccttcg aaggcttcaa tatcaagctg    2160
actgtaacat ccgagagcct agccgaactg aacaagccag tgcccccaa gcccccaaat     2220 gtcaacagac cagtcaacac tgggggactc aaggcagtca gcaacgccct caagaccggt    2280
cgatacagga acgaagccgg actgagtggt ctcgtccttc tagccacagc aagaagccgt    2340
ctgcaagacg cagttaaggc caaggcagaa gccgagaaac tccacaggtc caagcctgac    2400
gaccccgatg cagactggtt tgaaagatca gaaactctgt cagaccttct ggagaaagcc    2460
gacatcgcca gcaaggtcgc ccactcagca ctcgtggaaa caagcgacgc tcttgaagca    2520
gttcagtcga cttccgtgta caccccaag tacccagaag tcaagaaccc acagaccgcc     2580
tccaaccccg ttgttgggct ccacctgccc gccaagagag ccaccggtgt ccaggccgct    2640
cttctcggag caggaacgag cagaccaatg gggatggagg ccccaacacg gtccaagaac    2700
gccgtgaaaa tggccaaacg gcggcaacgc caaaaagaga gccgccaata gccatgatgg    2760
gaaccactca agaagaggac actaatccca gaccccgtat ccccggcctt cgcctgcggg    2820
ggccccc                                                              2827

<210> SEQ ID NO 5
<211> LENGTH: 3261
<212> TYPE: DNA
<213> ORGANISM: Artificial
<220> FEATURE:
<223> OTHER INFORMATION: synthetic construct

<400> SEQUENCE: 5
ggatacgatc ggtctgaccc cggggagtc acccggggac aggccgtcaa ggccttgttc     60
caggatggga ctcctccttc tacaacgcta tcattgtagg ttagtagaga tcagacaaac    120
gatcgcagcg atgacaaacc tgcaagatca aacccaacag attgttccgt tcatacggag    180
ccttctgatg ccaacaaccg gaccggcgtc cattccggac dacaccctgg agaagcacac    240
tctcaggtca gagacctcga cctacaattt gactgtgggg gacacagggt cagggctaat    300 tgtcttttc cctggattcc ctggctcaat tgtgggtgct cactacacac tgcagagcaa     360
tgggaactac aagttcgatc agatgctcct gactgcccag aacctaccgg ccagctacaa    420
ctactgcagg ctagtgagtc ggagtctcac agtaaggtca agcacactcc ctggtggcgt    480
ttatgcacta acggcacca taaacgccgt gaccttccaa ggaagcctga gtgaactgac     540
agatgttagc tacaatgggt tgatgtctgc aacagccaac atcaacgaca aaattgggaa    600
cgtcctagta ggggaagggg ttactgtcct cagcttaccc acatcatatg atcttgggta    660
tgtgaggctt ggtgacccca ttcccgcaat agggcttgac ccaaaaatgg tagccacatg    720
tgacagcagt gacaggccca gagtctacac cataactgca gccgatgatt accaattctc    780
atcacagtac caaccaggtg gggtaacaat cacactgttc tcagccaaca ttgatgccat    840
cacaagcctc agcgttgggg gagagctcgt gtttcaaaca agcgtccacg gccttgtact    900
gggcgccacc atctacctta taggctttga tgggtctgcg gtaatcacta gagctgtggc    960
cgcaaacaat gggctgacga ccggcaccga caatctatg ccattcaatc ttgtgattcc    1020
```

-continued

```
aaccaacgag ataacccagc caatcacatc catcaaactg gagatagtga cctccaaaag      1080
tggtggtcag gaaggggacc agatgtcatg gtcggcaagt gggagcctag cagtgacgat      1140
tcatggtggc aactatccag gggccctccg tcccgtcaca ctagtggcct acgaaagagt      1200
ggcaacagga tccgtcgtta cggtcgctgg ggtgagcaac ttcgagctga tcccaaatcc      1260
tgaactagca aagaacctgg ttacagaata cggccgattt gacccaggag ccatgaacta      1320
cacaaaattg atactgagtg agagggaccg tcttggcatc aagaccgtct ggccaacaag      1380
ggagtacact gactttcgtg aatacttcat ggaggtggcc gacctcaact ctcccctgaa      1440
gattgcagga gcattcggct tcaaagacat aatccgggcc ataaggagga tagctgtgcc      1500
ggtggtctcc acattgttcc cacctgccgc tcccctagcc catgcaattg gggaaggtgt      1560
agactacctg ctgggcgatg aggcacaggc tgcttcagga actgctcgag ccgcgtcagg      1620
aaaagcaaga gctgcctcag gccgcataag gcagctgact ctcgccgccg acaaggggta      1680
cgaggtagtc gcgaatctat tccaggtgcc ccagaatccc gtagtcgacg ggattcttgc      1740
ttcacctggg gtactccgcg gtgcacacaa cctcgactgc gtgttaagag agggtgccac      1800
gctattccct gtggttatta cgacagtgga agacgccatg acacccaaag cattgaacag      1860
caaaatgttt gctgtcattg aaggcgtgcg agaagacctc caacctccat ctcaaagagg      1920
atccttcata cgaactctct ctggacacag agtctatgga tatgctccag atggggtact      1980
tccactggag actgggagag actacaccgt tgtcccaata gatgatgtct gggacgacag      2040
cattatgctg tccaaagatc ccatacctcc tattgtggga aacagtggaa atctagccat      2100
agcttacatg gatgtgtttc gacccaaagt cccaatccat gtggctatga cgggagccct      2160
caatgcttgt ggcgagattg agaaagtaag ctttagaagc accaagctcg ccactgcaca      2220
ccgacttggc cttaggttgg ctggtcccgg agcattcgat gtaaacaccg ggcccaactg      2280
ggcaacgttc atcaaacgtt tccctcacaa tccacgcgac tgggacaggc tcccctacct      2340
caacctacca taccttccac ccaatgcagg acgccagtac caccttgcca tggctgcatc      2400
agagttcaaa gagaccccccg aactcgagag tgccgtcaga gcaatggaag cagcagccaa      2460
cgtggaccca ctattccaat ctgcactcag tgtgttcatg tggctggaag agaatgggat      2520
tgtgactgac atggccaact tcgcactcag cgacccgaac gcccatcgga tgcgaaattt      2580
tcttgcaaac gcaccacaag caggcagcaa gtcgcaaagg gccaagtacg ggacagcagg      2640
ctacggagtg gaggctcggg gccccacacc agaggaagca cagagggaaa aagacacacg      2700
gatctcaaag aagatggaga ccatgggcat ctactttgca acaccagaat gggtagcact      2760
caatgggcac cgagggccaa gccccggcca gctaaagtac tggcagaaca cacgagaaat      2820
accggaccca aacgaggact atctagacta cgtgcatgca gagaagagcc ggttggcatc      2880
agaagaacaa atcctaaggg cagctacgtc gatctacggg gctccaggac aggcagagcc      2940
accccaagct ttcatagacg aagttgccaa agtctatgaa atcaaccatg acgtggcccc      3000
aaaccaagaa cagatgaaag atctgctctt gactgcgatg gagatgaagc atcgcaatcc      3060
caggcgggct ctaccaaagc ccaagccaaa acccaatgct ccaacacaga dacccccctgg      3120 tcggctgggc cgctggatca ggaccgtctc tgatgaggac cttgagtgag ctcctgggga      3180
gtctcccgac accacccgcg caggtgtgga caccaattcg gccttacaac atcccaaatt      3240
ggatccgttc gcgggtcccc t                                               3261
```

IN OVO VACCINE AGAINST INFECTIOUS BURSAL DISEASE

CROSS-REFERENCE TO RELATED APPLICATION

The subject matter of the present application relates to and encompasses the disclosure of U.S. Provisional Patent Application No. 60/693,505, filed on Jun. 23, 2005 in the name of Vikram Vakharia for "IN OVO VACCINE AGAINST INFECTIOUS BURSAL DISEASE." The disclosure of such provisional application is hereby incorporated herein by reference in its entirety, for all purposes.

BACKGROUND OF THE INVENTION

1. Field of the Invention

The present invention relates to a recombinant non-pathogenic infectious bursal disease virus (IBDV) and methods of delivering via in ova for protection against virulent challenge by classic and variant strains of IBDV.

2. Description of the Related Art

Infectious bursal disease virus (IBDV), a member of the Birnaviridae family, is the causative agent of a highly immunosuppressive disease in young chickens (Kibenge, et al., 1988). Infectious bursal disease (IBD) or Gumboro disease is characterized by the destruction of lymphoid follicles in the bursa of Fabricius. In a fully susceptible chicken flock of 3-6 weeks of age the clinical disease causes severe immunosuppression, and is responsible for losses due to impaired growth, decreased feed efficiency, and death. Susceptible chickens less than 3 weeks old do not exhibit outward clinical signs of the disease but have a marked infection characterized by gross lesions of the bursa.

IBDV is a pathogen of major economic importance to the nation and world's poultry industries. It causes severe immunodeficiency in young chickens by destruction of precursors of antibody-production B cells in the bursa of Fabricius. Immunosuppression causes increased susceptibility to other diseases, and interferes with effective vaccination against Newcastle disease, Marek's disease and infectious bronchitis disease viruses.

The capsid of the IBDV virion consists of several structural proteins. As many as nine structural proteins have been reported but there is evidence that some of these may have a precursor-product relationship. The designation and molecular weights of the viral proteins (VP) are as shown below.

| Viral Protein | Molecular Weight |
| --- | --- |
| VP1 | 90 kDa |
| VP2 | 41 kDa |
| VP3 | 32 kDa |
| VP4 | 28 kDa |
| VP5 (NS) | 17 kDa |

The IBDV genome consists of two segments of double-stranded (ds)RNA that vary between 2827 (segment B) to 3261 (segment A) nucleotide base pairs. The larger segment A encodes a 110-kDa precursor protein in a single large open reading frame (polyprotein ORF) which is cleaved by autoproteolysis to form the mature viral proteins VP2, VP3 and VP4 (Hudson, P. J. et al., 1986). VP2 and VP3 are the major structural proteins of the virion. VP2 is the major host-protective immunogen of IBDV, and contains the antigenic regions responsible for the induction of neutralizing antibodies (Azad, et al., 1987). A second open reading frame (ORF), preceding and partially overlapping the polyprotein gene, encodes a non structural (NS) protein (VP5).

It has been demonstrated that the VP2 protein is the major host protective immunogen of IBDV, and that it contains the antigenic region responsible for the induction of neutralizing antibodies. This region containing the neutralization site has been shown to be highly conformation-dependent. The VP3 protein has been considered to be a group-specific antigen because it is recognized by monoclonal antibodies directed against it from strains of both serotype I and II viruses. The VP4 protein appears to be a virus-coded protease that is involved in the processing of a precursor polyprotein of the VP2, VP3 and VP4 proteins.

In the past, control of IBDV infection in young chickens has been achieved by live vaccination with avirulent strains, or principally by the transfer of maternal antibodies induced by the administration of live and killed IBDV vaccines to breeder hens. The strategy for the control of IBDV in chicks involves hyperimmunization of breeders, which allows them to transmit high levels of maternal antibodies to progeny during the critical first few weeks of life. Although maternal antibodies provide protection during this period, continued protection against IBDV must be maintained before the maternal immunity reaches sub-protective levels by the administration of live vaccines. However, maternal antibodies can neutralize a vaccine virus and reduce the viral load needed to induce immunity (Sharma et al., 1987). In addition, new antigenic variants of IBDV, which appeared during the 1980's, introduced new problems for poultry production. These new field isolates were able to break through neutralizing maternal antibodies induced by standard IBDV vaccines (Snyder, 1992). Since then, these variant strains have been incorporated into commercial inactivated vaccines for broiler breeders. For example, Mundt et al., 2003 vaccinated broilers, in ovo, with a chimeric IBDV vaccine using epitopes from classic and E/Del variant viruses, however, the challenge induced chronic lesions in BF of the vaccinated broilers.

Unfortunately, despite these vaccination measures, IBDV continues to be a problem. Very virulent strains of IBDV have caused outbreaks of disease with high mortality in Europe and Asia (Nunoya et al., 1992; van den Berg et al., 1991) despite vaccination programs. In addition, live vaccines that are available for mass vaccination of broilers in the first few weeks of life are not suitable for in ovo administration. These vaccines may induce immunosuppression during late stages of incubation, when the embryo is highly susceptible to infection.

Thus, it would be advantageous to develop a vaccine comprising a recombinant virus that can be administered in ovo but is not susceptible to the shortcomings of previous vaccines such as inducing immunosuppression during late stages of incubation or being neutralized by maternal antibodies.

SUMMARY OF THE INVENTION

The present invention relates to a recombinant IBDV virus that is deficient in the expression of VP5 nonstructural protein (NS) and grows one log lower than the parental viruses, exhibits decreased cytotoxic and apoptotic effects in cell culture.

In yet another aspects, the present invention relates to a non-pathogenic vaccine comprising a recombinant IBDV comprising a Segment A designated as rD78GLSNSΔ (SEQ ID NO: 5) that includes nucleotide sequences from D78 and GLS strains and wherein the NS protein is not expressed.

In yet another aspect the present invention relates to an in ovo method of vaccination of poultry in the presence of maternal immunity against IBDV, the method comprising:

introducing in ovo a vaccine comprising a recombinant virus comprising at least Segment A (SEQ ID NO: 5) modified to include nucleotide sequences from D78 and GLS strains and wherein the NS protein is not expressed and the vaccine is delivered in an amount sufficient to protective against STC-IBDV challenge.

A further aspect of the present invention provides for a live, non-pathogenic recombinant IBD virus and method of producing same for use as a vaccine to protect against IBDV, the method comprising the following steps:

(a) preparing cDNA of infectious bursal disease virus genome segments A and B, wherein the segment A (SEQ ID NO: 5) is modified to prevent expression of NS protein, wherein the cDNA contains epitopic determinants from D78 and/or GLS strains;
(b) transcribing said cDNA to produce synthetic RNA transcripts,
(c) transfecting host cells with said synthetic RNA transcripts,
(d) incubating said host cells in a culture medium, and
(e) isolating live, nonpathogenic, infectious bursal disease virus from said culture medium.

Other aspects and features of the invention will be more fully apparent from the ensuing disclosure and appended claims.

BRIEF DESCRIPTION OF THE FIGURES

Figure 1:
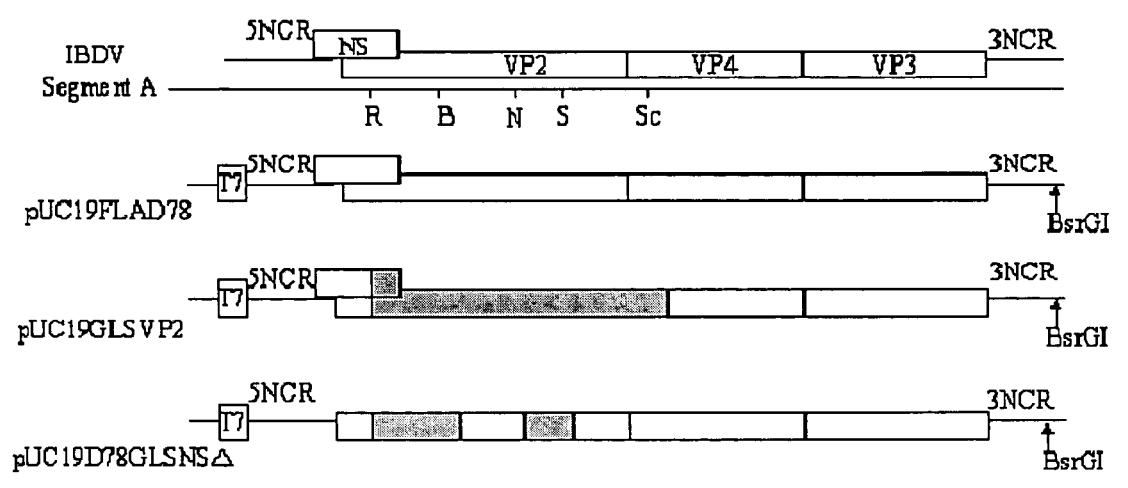

FIG. 1 shows cDNA constructs of D78 and GLS strains used to generate plus-sense RNA transcripts using T7 RNA polymerase. A map of the IBDV genome segment A, with its coding capacity, is shown at the top of the figure. Open boxes depict the coding regions of the D78 strain, whereas, the shaded boxes represent the coding regions of GLS strain. Selected restriction sites, important for the construction of chimeric cDNA clones of segment A, are shown in the figure: B, Bst EII; N, Nar I; Sc, Sac II; S, Spe I; R, Rsr II. All constructs contain a T7 polymerase promoter sequence at their 5'-end.

FIG. 4 shows amino acid and nucleotide sequences for Segment B of D78 and GLS strains.

FIG. 5 shows the chimeric nucleotide sequence of the Segment A used in the recombinant virus of the present invention.

DETAILED DESCRIPTION OF THE INVENTION

Figure 2:
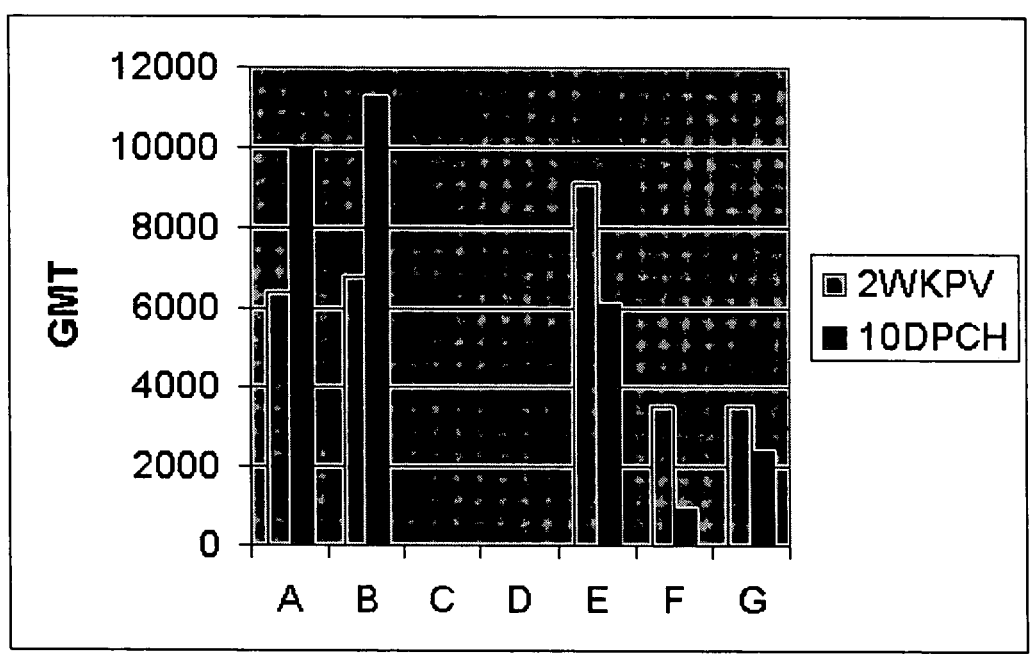
FIG. 2 shows the ELISA geometric mean titer (GMT) from two-week-old chickens post in ovo vaccination with rD78GLSNSΔ and 10 days post IBDV challenge. A) SPF embryos vaccinated with $5.6 \times 10^3$ pfu/egg of the vaccine; B) SPF embryos vaccinated with $2.3 \times 10^3$ pfu/egg of the vaccine; C) SPF embryos unvaccinated, but challenged at 2 weeks post in ovo vaccination; D) SPF embryos were neither vaccinated, nor challenged; E) broiler embryos vaccinated with $5.6 \times 10^3$ pfu/egg; F) broiler embryos unvaccinated, but challenged at 2 weeks post in ovo vaccination; G) broiler embryos unvaccinated, and non-challenged.

In an effort to aid in the control of this disease, a recombinant IBD vaccine virus that can protect against both classical and variant strains is described herein and which can generated by methods described in Liu, 2003. This recombinant virus, designated as rD78GLSNSΔ, is deficient in the expression of VP5 nonstructural protein (NS). It grows one log lower than the parental viruses, and exhibits decreased cytotoxic and apoptotic effects in cell culture. This virus fails to induce any pathological lesions in the bursa of infected three-week-old chickens. In addition, vaccinated birds challenged with classic (STC) and variant (GLS) strains of IBDV were fully protected.

"Epitopic determinants" as used herein is defined as amino acids or amino acid sequences which correspond to epitopes recognized by one or more monoclonal antibodies.

Briefly, the cDNA clone containing the preferred coding and/or non-coding regions of IBDV-RNA segment A and B can be prepared using standard cloning procedures and methods, as described for IBDV in Mundt, E., 1996, the contents of which are hereby incorporated herein by reference for all purposes. Manipulations of DNAs can be performed according to standard protocols (Sambrook, J., 1989).

To generate cDNA clones of a coding region of the desired structural proteins, the genomic RNA is used as a template for synthesizing and amplifying according to general RT-PCR techniques well known in the art. Specifically, U.S. Pat. No. 5,595,912 provides techniques applicable for cDNA amplifying in the present invention. The desired amplified fragments are then cloned into an expression vector.

Useful vectors for this purpose include plasmids, and viruses such as baculoviruses, herpes virus (HVT) and pox viruses, e.g., fowl pox virus, and the like. The vectors may also expression control sequences including, but not limited to, a promoter, enhancers, operators, inducers, ribosome binding sites, etc.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. Those promoters most commonly used in recombinant DNA construction include the beta.-lactamase (penicillinase) and lactose promoter systems and a tryptophan (TRP) promoter system. While these are the most commonly used, other microbial promoters have been discovered and utilized, and details concerning their nucleotide sequences have been published, enabling a skilled worker to introduce functional promoters into plasmid vectors.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

Also provided herein is a host cell transformed with the recombinant vector of the present invention or a host cell transfected with the synthetic RNA of the present invention. The host cell may be a eukaryotic or a prokaryotic host cell. Suitable examples are *E. coli*, insect cell lines such as Sf-9, chicken embryo fibroblast (CEF) cells, chicken embryo kidney (CEK) cells, African green monkey Vero cells and the like. Further, the host cell can be an insect cell or yeast cell that is transfected for expression of the desired protein(s).

Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection.

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA. The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* can be transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides. In yet another embodiment, the present invention contemplates a process of preparing a live IBDV of the present invention comprising transfecting cells with a polynucleotide that encodes for the Segment A and B, wherein the NS of Segment A is not expressed to produce transformed host cells; and maintaining the transformed host cells under biological conditions sufficient for expression of the virus. The transformed host cells can be eukaryotic cells or prokaryotic cells. Most preferably, transfection is accomplished using a hereinbefore disclosed expression vector. A variety of cells are amenable to a process of the invention, for instance, yeasts cells, human cell lines, and other eukaryotic cell lines known well to those of the art.

Also part of this invention is a NS protein deficient IBDV vaccine comprising a protecting amount of a recombinantly produced virus or portion of a virus, wherein the virus does not induce pathological lesions. A cDNA clone of IBDV segment A is constructed, in which the first and only initiation codon (ATG) of NS protein A is mutated to a stop codon (TAG).

The virus can be further modified or inactivated by chemical or physical means. Chemical inactivation can be achieved by treating the virus with, for example, enzymes, formaldehyde, .beta.-propiolactone, ethylene-imine or a derivative thereof, an organic solvent (e.g. halogenated hydrocarbon) and or a detergent. If necessary, the inactivating substance can be neutralized after the virus has been inactivated. Physical inactivation can be carried out by subjecting the viruses to radiation such as UV light, X-radiation, or gamma-radiation.

The virus can also be modified by known methods including serial passage, deleting further sequences of nucleic acids and site directed. mutagenesis either before or after production of the infectious virus.

The virus is a chimeric recombinant virus, which contains epitopic determinants for more than one strain of IBDV. Epitopic determinants as discussed in the present document are amino acids or amino acid sequences which correspond to epitopes recognized by one or more monoclonal antibodies. Methods for producing a chimeric virus are disclosed in Vakharia, 1997; Snyder et al., 1994, WO 95/26196, and Liu, 2003 the contents of which are incorporated by reference herein for all purposes.

A recombinant peptide is recovered or collected either from the transfected cells or the medium in which those cells are cultured. Recovery comprises isolating and purifying the recombinant polypeptide. Isolation and purification techniques for polypeptides are well known in the art and include such procedures as precipitation, filtration, chromatography, electrophoresis and the like. For instance, the immunogenic polypeptides can be harvested using conventional techniques described in Dobos et al., 1979.

These virus polypeptides can be used to prepare vaccines which will confer protection on inoculated poultry, in particular, chickens, and in a preferred embodiment, broiler chickens, protection against challenge from each IBDV bearing an epitope reflected in the plurality of epitopic determinants present in the inoculum. Thus, a single immunogen gives rise to immunity against a variety of IBDV strains while remaining non-pathogenic to poultry.

The administration of the vaccines can be effectively done according to well-established procedures. Preferably, the vaccine is injected in ovo to embryonated eggs, such as 14-18 day-old embryonated eggs.

The vaccine of the present invention is administered to poultry to prevent IBD anytime before or after hatching. Preferably, the vaccine is administered prior to the time of birth and after the animal is about 6 weeks of age. Poultry is defined to include but not be limited to chickens, roosters, hens, broilers, roasters, breeders, layers, turkeys and ducks.

Also included within the scope of the present invention are nucleic acid sequences encoding the recombinant virus of the present invention.

In another aspect, the present invention contemplates a process of producing an antibody immunoreactive with the recombinant virus of the present invention, comprising the steps of (a) transfecting recombinant host cells with polynucleotides that encode the recombinant virus, (b) culturing the host cells under conditions sufficient for expression of the peptides; (c) recovering the peptides; and (d) preparing antibodies to the peptides.

Typically, a monoclonal antibody of the present invention can be readily prepared by a technique which involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine. This culturing provides a population of hybridomas from which specific hybridomas are selected. Typically, selection of hybridomas is performed by culturing the cells by single-clone dilution in microliter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1-200 ug of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium* tuberculosis). At some time (e.g., at least two weeks) after the first injection, mice are boosted by injection with a second dose of the antigen mixed with incomplete Freund's adjuvant. A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture. Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media. Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

Yet another aspect of the present invention provides for pharmaceutical compositions comprising the recombinant live nonpathogenic virus of the present invention in combination with a physiologically acceptable carrier.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil can be employed including synthetic mono- or di-glycerides. In addition, fatty acids such as oleic acid find use in the preparation of injectables.

The foregoing aspects and embodiments of the present invention are further described in the following Examples. However, the present invention is not limited by the Examples, and variations will be apparent to those skilled in the art without departing from the scope of the present invention.

EXAMPLES

The potential use of this recombinant attenuated virus was evaluated in ovo to determine ability to protect SPF as well as commercial chicks from IBDV challenges. Fertile eggs were obtained from a local poultry farm that routinely immunizes broiler breeders with live and inactivated vaccines to confer high levels of maternal antibodies to the progeny. The vaccination program for these breeders consisted of one live IBDV vaccination at 4 weeks of age, and booster vaccinations at 10 and 18 weeks of age with an inactivated oil-emulsion vaccine containing standard and variant strains of IBDV.

Two different doses of this recombinant vaccine were evaluated in SPF eggs in the absence of maternal antibodies. A full dose was used to vaccinate broiler embryos with maternal antibodies to verify its ability to break through antibody barrier and generate a protective immune response against IBDV challenges.

Materials and Methods:

Vero cells were maintained in M199 medium supplemented with 5% fetal bovine serum (FBS) at 37° C. in a humidified 5% $CO_2$ incubator, and used for propagation of the virus and transfection experiments. Primary chicken embryo fibroblast (CEF) cells were prepared from 10-day-old embryonated eggs (SPAFAS, Inc., Storrs, Conn.), as described previously in Mundt, et al, 1996. Secondary CEF cells were maintained in a growth medium consisting of M199 and F10 (50%/50% v/v) and 5% FBS, and used for immunofluorescence, virus titration and plaque assays. D78, GLS and the recovered chimeric IBDV were titrated in secondary CEF cells as described by Yao, et al., 1998. A tissue culture adapted GLS-5 strain of IBDV (GLS-TC) was propagated in CEF cells. A panel of MAbs, prepared against various strains of IBDV, was used to characterize IBDV antigens by AC-ELISA, as described previously by Vakharia, et al. 1994.

Construction of Full-Length cDNA Clones:

All manipulations of DNAs were performed according to standard protocols. Construction of full-length cDNA clones of IBDV genomic segments of strain D78 (with sequence tags), pUCD78NSΔ, pUCD78B or GLS strain (pGLS-5), has been described previously by Vakharia, et al. 1994; Yao, et al., 1998; and Mundt, et al., 1996. Plasmid pUC19GLSVP2 was prepared by replacing an RsrI-SacII fragment in plasmid pUC19FLAD78 with respective RsrI-SacII fragment derived from plasmid pGLS-5. To generate an NS-deficient IBDV, plasmid pUCD78NSΔGLSVP2 was first prepared by inserting an RsrI-SacII fragment of GLS in plasmid pUCD78NSΔ. This plasmid was then used as a vector by digesting with BstEII and SacII enzymes. As shown in FIG. 1, the GLS-specific sequences from BstEII-NarI and SpeI-SacII sites were replaced with the D78 sequences to obtain plasmid pUC19D78GLSNSΔ. DNA from these plasmids was sequenced by dideoxy chain termination method, using an Automated DNA Sequencer (Applied Biosystem). The integrity of the full-length constructs was tested by in vitro transcription and translation coupled reticulocyte lysate system using T7 RNA polymerase (Promega Corp.). The resulting labeled products were separated by a 12.5% SDS-PAGE and visualized by autoradiography (data not shown).

Transcription and Transfection of Synthetic RNAs:

Transcription of synthetic RNAs, transfection of Vero cells, and characterization of recovered IBDV was carried out essentially as described earlier by Mundt, et al, 1996; and Yao, et al., 1998. Briefly, plasmid pUC19D78GLSNSΔ and pUCD78B were digested with BsrGI or PstI enzymes, respectively (FIG. 1). The combined RNAs, derived from cDNA clones of segments A and B, were used for transfection in Vero cells. The recovered virus was designated as recombinant D78GLSNSΔ (rD78GLSNSΔ).

Plaque Assays:

Virus stocks propagated in cell culture were titered by plaque assay as described by Mundt, et al. 1996. Briefly, the infected supernatant was diluted in ten-fold increments in MEM without FCS. Confluent monolayers of CEFs were infected with serial dilutions of viruses ($10^{-4}$ to $10^{-7}$, 0.1 mL/well). After 1 h adsorption at RT, the media was removed and the monolayer overlaid with 3 mL of 1% SeaPlaque agarose (Difco) containing 10% tryptose phosphate broth, 2% FCS, 0.112% $NaHCO_3$, 100 unit/mL penicillin, 100 μg/mL streptomycin and 0.25 μg/mL fungizone. On day 3, the agarose overlay was removed and cells were fixed with formalin. After fixing, the cells were stained with crystal violet and plaques were counted and expressed as plaque forming units (pfu/mL).

Experimental Design:

The experimental groups and controls are shown in Table 1. A larger number of eggs were utilized for treatment groups A, B, and E (vaccinated) because of a possible adverse effect due to vaccination. Sample size was calculated accordingly to protocol previously approved. SPF and commercial fertile broiler eggs of 18 days of embryonation were inoculated using a full dose of rIBDV (group A, and E). Each embryo received $5.6 \times 10^3$ pfu/0.2 mL of rD78GLSNSΔ. Another group of SPF eggs received only half a dose of this virus, which was $2.3 \times 10^3$ pfu/0.2 mL (group B). The negative controls consisted of non-vaccinated, unchallenged SPF and commercial embryos (groups D, and G). The challenge control groups consisted of SPF and commercial eggs, which did not receive the vaccine and were challenged two weeks post-vaccination (groups C, and F). After in ovo vaccination, all eggs were sealed with adhesive tape and re-incubated.

TABLE 1

Experimental design to evaluate live attenuated rIBDV vaccine.

| Group | Egg type | Vaccine dose[a] (pfu) | # of eggs |
|---|---|---|---|
| A | SPF[b] | $5.6 \times 10^3$ | 27 |
| B |  | $2.3 \times 10^3$ | 27 |
| C |  | NV/CH[c] | 17 |
| D |  | NV/NCH[d] | 17 |
| E | Broilers[e] | $5.6 \times 10^3$ | 24 |
| F |  | NV/CH | 9 |
| G |  | NV/NCH | 9 |

[a]8-day-old embryos received 0.2 mL of rIBDV vaccine containing either $5.6 \times 10^3$ or $2.3 \times 10^3$ pfu.
[b]specific-pathogen-free fertile eggs.
[c]non-vaccinated, challenged control group.
[d]non-vaccinated, non-challenged control group.
[e]fertile broiler eggs from a poultry farm.

The SPF embryos were free of any other immunosuppressive diseases that could compromise the results, such as adenoviruses, and chicken anaemia virus. The commercial eggs were obtained from Sunrise farms, Catskill, N.Y.

After 21 days of incubation, all hatched chicks were housed in BL-2 isolators at Gudelsky Veterinary Center. Two weeks post-hatch, all birds were bled and challenged with STC strain (0.2 mL by the ocular and nasal route-$10^3$ $EID_{50}$) of IBDV, except group D, and G. At ten days post-challenge, all the remaining birds were anesthetized, bled, and humanely euthanized. Spleen and bursa were collected and bursa/body weight recorded. The bursae were sectioned in half. Spleen and bursa halves were placed in 10% buffered formalin for histology. The other half of the bursa was stored frozen for later testing by antigen capture-ELISA (AC-ELISA).

The antibody levels in serum samples collected at 2 weeks post-vaccination, and 10 days post-challenge, were determined by ELISA and virus neutralization (VN). A commercial ELISA kit was used (Synbiotics, San Diego, Calif.). The frozen bursae were processed as described earlier and probed for antigen detection by AC-ELISA (Synbiotics, San Diego, Calif.). Fixed tissues were sectioned at American Histolabs (Gaithersburg, Md.) and stained by hematoxylin-eosin (HE).

Virus Neutralization Assay (VN):

Serum samples were heat-inactivated at 56° C. for 1 h and diluted in serial two-fold dilutions. Each dilution was mixed with 100 $TCID_{50}$ of rIBDV and incubated for 1 h at 37° C. The mixture was added to 85-90% confluent monolayer of Vero cells, grown in 96-well tissue culture plates (Costar, Ithaca, N.Y.). All plates were incubated for 5-6 days until the presence of CPE was detected in the virus control wells. Normal serum from SPF birds was used as a negative control and a polyclonal anti-IBDV (SPAFAS) was used as a positive control. Anti-IBDV titers were determined 5-6 days later, averaged, and expressed as $\log_2$.

Results:

Vaccine Safety:

Hatchability and first week survival rates are shown in Table 2. The hatchability rates in SPF eggs from group A and B were similar (92.5%), indicating that the vaccine is safe even when higher doses were administered. The percentages of hatched birds and first week survival were not significantly different from vaccinated groups and control non-vaccinated. The hatchability rates in broilers were lower than SPF embryos and this is evident in both vaccinated and non-vaccinated birds (88.8%). This reduction in hatchability is attributed to stress caused by temperature shock during transportation. Embryonated eggs were removed from incubators at 37° C. and transported at 22° C. for 2 h. However, the hatchability in this experiment is much higher than the average observed in the poultry industry (83%) because all unviable eggs were discarded prior to in ovo vaccination.

TABLE 2

Effect of in ovo vaccination of rIBDV on hatchability and survival of hatched chicks.

| Group | Egg type | # of chicks hatched (%) | 1$^{st}$ week survival rate (%) |
| --- | --- | --- | --- |
| A | SPF | 25/27 (92.5)$^a$ | 24 (96) |
| B | | 25/27 (92.5) | 25 (100) |
| C | | 16/17 (94.1) | 16 (100) |
| D | | 17/17 (100) | 17 (100) |
| E | Broilers | 18/24 (75) | 17 (94.4) |
| F | | 7/9 (77.8) | 7 (100) |
| G | | 8/9 (88.8) | 8 (100) |

$^a$percentage of hatched chicks after in ovo vaccination with rIBDV.

Vaccine protection: Results of the IBDV challenge studies are shown in Table 3. All vaccinated birds were fully protected against IBDV-STC. The bursa/body weight ratio was calculated as bursa weight/body weight×1000. The vaccinated group was considered protected if all bursa/body weight ratios were equal or higher than 2SD (standard deviation) of the non-vaccinated, non-challenged control group. The mean for the SPF control (group D) was 5.35 (2SD=2.48). Thus, all SPF vaccinated birds with either dose were considered protected. Additionally, vaccinated broilers were also considered fully protected.

Table 3 also shows results from antigen detection assessed by AC-ELISA (Synbiotics, San Diego, Calif.) seven days post-challenge. IBDV antigen was detected in two SPF birds that were vaccinated with full dose of the vaccine. Viral antigens could not be detected in the BF of birds that received half dose of the vaccine or in broilers that received full dose. Antigen was detected in SPF challenge control group (11/12). As expected, no IBDV antigen could be detected in the negative control birds (group D, and G), whereas non-vaccinated, challenged broilers (8/9) were positive by AC-ELISA at 10 days post-challenge.

TABLE 3

Protection indices from birds vaccinated with rIBDV-attenuated vaccine and challenged with the classic STC strain of IBDV.

| Group | Birds with clinical signs/Challenged$^a$ | B/B weight$^b$ | AC-ELISA$^c$ | VN Log2$^d$ | | Lesion Score |
| --- | --- | --- | --- | --- | --- | --- |
| A | 0/20$^e$ (100)$^f$ | 6.04 ± 1.2$^g$ | 2/12 | 8.76 | 7.90 | 2.0 |
| B | 0/18 (100) | 5.27 ± 1.5 | 0/11 | 9.25 | 5.47 | 0 |
| C | 12/12 (NA)$^h$ | 4.31 ± 1.1 | 11/12 | 4.00 | 2.33 | 5.0 |
| D | 0/12 (NA) | 5.35 ± 1.2 | 0/12 | 3.16 | 4.00 | 0 |
| E | 0/17 (100) | 2.14 ± 0.8 | 0/11 | 9.46 | 7.58 | 0 |
| F | 10/12 (NA) | 1.48 ± 0.6 | 8/9 | 5.3 | 6.8 | 4.6 |
| G | 0/12 (NA) | 2.31 ± 0.5 | 0/9 | 5.4 | 6.8 | 0 |

$^a$at two weeks post-vaccination birds received 0.2 mL of $10^3$EID50% of IBDV-STC challenge.
$^b$(bursa weight/body weight) × 1000.
$^c$number of birds that had antigen detected as measured by antigen capture ELISA.
$^d$virus neutralization results two weeks post-vaccination and ten days post-challenge.
$^e$number of birds dead/number of birds challenged.
$^f$percentage of protected birds.
$^g$mean of bursa/body weight rations and standard deviation.
$^h$not applicable.

Antibody Responses:

The antibody responses as measured by commercial ELISA are shown in FIG. 2. At two weeks post-vaccination, all vaccinated groups had significantly higher antibody titers ($p<0.05$) than non-vaccinated groups by either test. As expected, all non-vaccinated SPF birds had negative titers for IBDV at 2 weeks post-vaccination. The non-vaccinated, commercial broilers had maternal antibody titers ranging from 455 to 5455 at 2 weeks of age. At 10 days post-challenge, all SPF vaccinated groups (full and half dose) showed significantly ($p<0.05$) higher titers than the same groups at two weeks post-vaccination. However, broilers receiving a full vaccine dose did not show an antibody increase after challenge as measured by ELISA. Antibody responses at 2 weeks post-vaccination in SPF birds that received half dose of the vaccine were relatively higher than SPF birds vaccinated with a full dose. The level of protective maternal antibodies in the non-vaccinated, unchallenged broilers seemed to wane slightly after challenge. Antibody responses were not detected in SPF non-vaccinated, challenged control birds after 10 days of challenge. This result is expected considering that a primary immune response would take at least 2 weeks to be detected.

The results from virus neutralization assay are expressed as log2 in Table 3. All vaccinated groups showed protective levels (between 4-6 log2) of antibodies 2 weeks post-vaccination. Non-vaccinated control broilers showed maternal antibody levels (4.8 log2) lower than normal for the first few weeks of life. All control groups continued to exhibit only low levels of antibodies 10 days post-challenge. As expected, all vaccinated SPF birds showed higher humoral responses after challenge. Vaccinated broilers also showed higher antibody response 10 days post-challenge (7.5 to 9.46).

Figure 3:
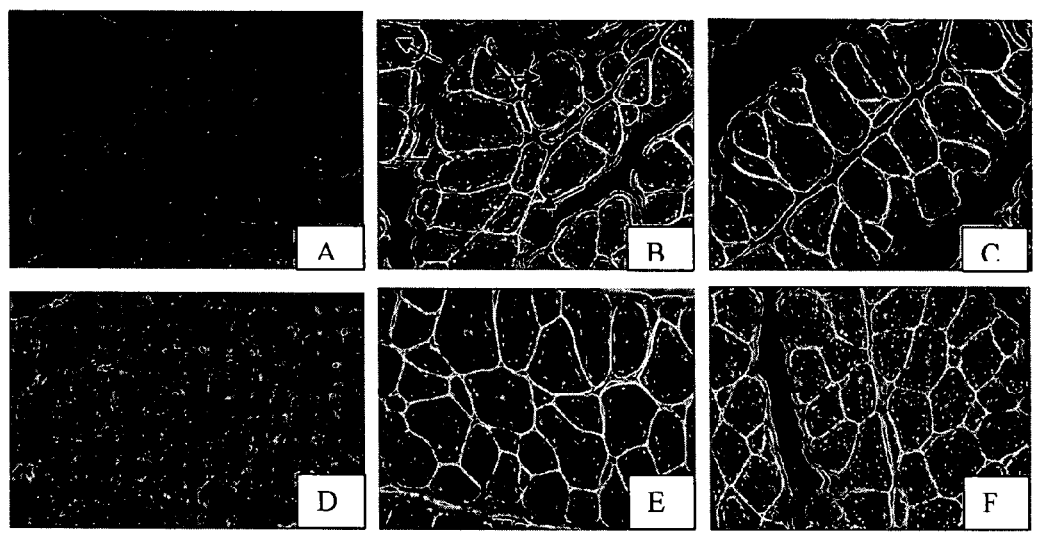
FIG. 3 shows sections of the BF stained by hematoxylin-eosin for histopathological examination 10 days post-challenge with IBDV-STC. Eighteen-day-old embryos were inoculated with either $5.6 \times 10^3$ pfu (full dose) or $2.3 \times 10^3$ pfu (half dose) of rD78GLSNSΔ. A) non-vaccinated, challenged SPF, shows severe lymphocytic necrosis and heterophilic inflammation; B) vaccinated (full dose) and challenged SPF birds shows lymphocytic depletion (indicated by arrows); C) vaccinated (half dose) and challenged SPF shows no visible microscopic lesions; D) non-vaccinated, challenged broiler shows lymphocytic necrosis and loss of follicular structure; E) unvaccinated, and non-challenged control broiler shows no microscopic lesions; F) vaccinated (full dose) and challenged broiler shows no microscopic lesions.

Histopathology:

The averages of microscopic lesions are shown in Table 3. At 2 weeks post-vaccination, birds from the control and treatment groups that received either full dose or half dose did not show microscopic lesions in the BF. At 10 days post-challenge, SPF non-vaccinated birds that were challenged showed severe lymphocyte depletion, undulation in the epithelium, intra and interfollicular epithelial cysts, and degeneration of follicular structure (FIG. 3A, Table 3-C). SPF birds that received full dose of the vaccine (FIG. 3B) showed a mild degree of B-cell depletion, localized in a few follicles. The lesion score for this group was 2.0. SPF birds vaccinated with a half dose of the vaccine did not show histopathological lesions in the bursa (FIG. 3C, Table 3-B). The control non-vaccinated, challenged broilers showed bursal lesions. However, they were much milder than SPF challenged controls (FIG. 3D, Table 3-F). In addition, broilers that received a full dose of the vaccine showed normal bursae after 10 days post IBDV challenge (FIG. 3F, Table 3-E).

The spleens of SPF non-vaccinated, challenged birds showed hemorrhages and lymphocytic depletion. Non-vaccinated broilers that were challenged showed a milder but more generalized reduction of lymphocytes throughout the entire organ. No lesions were observed in the spleens from vaccinated groups (data not shown).

Described herein is a recombinant live attenuated vaccine that expresses multiple neutralizing epitopes of classical and variant strain of IBDV. The vaccine was evaluated in 18-day-old SPF and commercial embryos. SPF embryos were injected with a full or half dose of the virus through the amniotic cavity. Two weeks post-vaccination, birds were challenged with an IBDV-STC strain. Commercial broilers vaccinated with a full dose and SPF embryos vaccinated with half dose were fully protected. In addition, no significant microscopic bursal lesions were observed in these groups. Interestingly, SPF birds that received a full dose of the vaccine in ovo exhibited microscopic lesions similar to unvaccinated challenged control group.

No detrimental effects on hatchability with either dosage used were observed. However, histopathological results suggested that a higher dose of the vaccine given to birds that lack sufficient maternal antibody may still be virulent even though clinical signs of IBD were not observed. These findings agree with previous research in SPF and broiler embryos vaccinated with three commercial intermediate vaccines in ovo. Microscopic bursal lesions were observed even when half of the recommended dose was used (Giambrone et al., 2001).

In a previous report, microscopic lesions were not observed when a full dose of rIBDV live attenuated virus was used to vaccinate two-week-old chickens ocularly (Liu, 2003). In the present application, bursal lesions were observed in SPF birds, lacking maternal antibodies that received a full dose of the vaccine when delivered in ovo. At 10 and 15 days of embryonation, prebursal stem cells are migrating via the blood supply from the spleen to the BF (Masteller et al., 1994). Consequently, at eighteen days of incubation, when in ovo vaccination occurred, the avian immune system was not fully developed and a viral infection that targets this organ may have caused irreversible damage.

Notably, vaccinated broilers had significant higher antibody titers than non-vaccinated broiler control group at two weeks post vaccination. According to Lutticken et al., 1994, these findings indicate that the vaccine was able to breakthrough maternal antibody barrier and seroconvert. Similar results were obtained in broilers vaccinated with a chimeric IBDV vaccine 14 days post-vaccination (Mundt et al., 2003). However, in the Mundt, et al. results, the challenge using classic and variant viruses induced chronic lesions in BF of vaccinated broilers with a chimeric virus expressing classic and variant epitopes of E/Del and D78 IBDV strains (Mundt et al., 2003).

Thus, it has been shown herein that use of rD78GLSNSΔ can be used as a vaccine for in ovo delivery, wherein the vaccine is safe, highly immunogenic, and protective against STC-IBDV challenge. Importantly, this recombinant virus was not neutralized by the maternal antibodies present in the embryo because a higher dose of the virus could be used and it replicated efficiently in ovo without affecting the viability of an embryo (since it is attenuated by lack of 17-kDa non-structural protein expression). Notably, at this dose, the wild type IBD virus would cause mortality of the embryonating egg.

REFERENCES

All reference cited herein are hereby incorporated by reference herein for all purposes.

Azad, A. A., Barrett, S. A. & Fahey, K. J. (1985). The characterization and molecular cloning of the double-stranded RNA genome of an Australian strain of infectious bursal disease virus. *Virology*, 143(1), 3544.

Dobos, P. (1979). Peptide map comparison of the proteins of infectious bursal disease virus. *J. Virol.*, 32(3), 1047-1050.

Giambrone, J. J., Dormitorio, T., Brown, T. (2001). Safety and efficacy of in ovo administration of infectious bursal disease viral vaccines. Avian Dis., 45:144-148.

Hudson, P. J., McKern, N. M., Power, B. E. & Azad, A. A. (1986). Genomic structure of the large RNA segment of infectious bursal disease virus. *Nucleic Acids Res*, 14(12), 5001-5012.

Kibenge, F. S., Dhillon, A. S. & Russell, R. G. (1988). Biochemistry and immunology of infectious bursal disease virus. *J Gen Virol*, 69(Pt 8), 1757-1775.

Liu, M. (2003). Pathogenesis and apoptosis study of infectious bursal disease virus (IBDV) and development of a bivalent IBDV vaccine. Ph.D. dissertation. University of Maryland, College Park, Md.

Lutticken et al., 1994,Lutticken D., van Loon A. A. W. M., de Vries M. J. H. S. (1994). Determination of the breakthrough titre of IBD vaccines or IBD challenge strains in MDA+chicken. In Proceedings of the International Symposium on Infectious Bursal Disease and Chicken Infectious Anaemia. Rauischholzhausen, Germany, p 272-278.

Masteller, E. L., Thompson, C. B. (1994). B cell development in the chicken. Poultry Sci., 73:998-1011.

Mundt, E., de Haas, N., van Loon, A. A. W. M. (2003). Development of a vaccine for immunization against classical as well as variant strains of infectious bursal disease virus using reverse genetics". Vaccine, 21:4616-4624.

Mundt, E. & Vakharia, V. N. (1996). Synthetic transcripts of double-stranded Birnavirus genome are infectious. *Proc Natl Acad Sci USA,* 93(20), 11131-11136.

Nunoya, T., Otaki, Y., Tajima, M., Hiraga, M., Saito, T. (1992). Occurrence of acute infectious bursal disease with high mortality in Japan and pathogenicity of field isolates in specific-pathogen-free chickens. Avian Dis., 36:597-609.

Sambrook, J., E. F. Fritsch, and T. Maniatis. (1989). Molecular Cloning a laboratory manual.2nd ed. Cold Spring Harbor Laboratory. Cold Spring Harbor. N.Y.

Sharma, J. M. (1987). Embryo vaccination of chickens with turkey herpesvirus: characteristics of the target cell of earl viral replication in embryonic lung. Avian Path., 16:567-579.

Snyder, D. B., Vakharia, V. N. & Savage, P. K. (1992). Naturally occurring-neutralizing monoclonal antibody escape variants define the epidemiology of infectious bursal disease viruses in the United States. *Arch Virol,* 127(1-4), 89-101.

Snyder, D. B., Vakharia, V. N., Mengel-whereat, S. A., et al., (1994). Active cross-protection induced by a recombinant baculovirus expressing chimeric infectious bursal disease virus structural proteins, *Avian Diseases* 38 (4): 701-707.

Vakharia, V. N. 1997, Biotechnology Annual Review Volume 3, 151-168.

Vakharia, V. N., He, J., Ahamed, B. & Snyder, D. B. (1994). Molecular basis of antigenic variation in infectious bursal disease virus. *Virus Res,* 31(2), 265-273.

Van den Berg, T. P., Gonze, M., Meulemans, G. (1991). "Acute infectious bursal disease virus in poultry: isolation and characterization of a highly virulent strains". Avian Pathol., 20:133-143.

WO 95/26196

Yao, K., Goodwin, M. A. & Vakharia, V. N. (1998). Generation of a mutant infectious bursal disease virus that does not cause bursal lesions. *J Virol,* 72(4), 2647-2654.

---

That which is claimed is:

1. A recombinant Infectious Bursal Disease virus (IBDV) in ovo in a poultry ovum containing poultry maternal antibodies, comprising at least SEQ ID NO: 5 as Segment A of the IBDV, wherein SEQ ID NO: 5 includes nucleotide sequences from D78 of and GLS strains, and wherein SEQ ID NO: 5 does not express a NS protein.

2. A non-pathogenic vaccine in an embryonated poultry egg, said non-pathogenic vaccine comprising a recombinant IBDV comprising at least SEQ ID NO: 5 as Segment A of the IBDV, wherein SEQ ID NO: 5 includes nucleotide sequences from D78 and GLS strains, wherein the recombinant IBDV is not neutralized by maternal antibodies present in an embryo of said embryonated poultry egg, wherein the recombinant IBDV is non-lethal to said embryo, and wherein SEQ ID NO: 5 does not express a NS protein.

3. An in ova method of vaccination of poultry in the presence of maternal immunity against IBDV, the method comprising:
   introducing in ovo a vaccine comprising a recombinant Infectious Bursal Disease virus (IBDV) comprising at least Segment A (SEQ ID NO: 5) modified to include nucleotide sequence from D78 and GLS strains, and wherein SEQ ID NO. 5 does not express a NS protein and wherein the vaccine is delivered in an amount sufficient to protect against STC-IBDV challenge.

4. A live, non-pathogenic recombinant IBD virus in ovo in a poultry ovum containing poultry maternal antibodies, wherein the live, non-pathogenic recombinant IBD virus is present in said ovum in a sufficient amount to protect the ovum against IBD challenge in the presence of said poultry maternal antibodies, and wherein the live, non-pathogenic recombinant IBD virus has been produce by the method comprising the following steps:
   (a) preparing cDNA of infectious bursal disease virus genome segments A and B, wherein the segment A comprises SEQ ID NO: 5 wherein the cDNA contains epitopic determinants from D78 and/or GLS strains, and wherein SEQ ID NO. 5 does not express a NS protein;
   (b) transcribing said cDNA to produce synthetic RNA transcripts,
   (c) transfecting host cells with said synthetic RNA transcripts,
   (d) incubating said host cells in a culture medium, and
   (e) isolating live, nonpathogenic, infectious bursal disease virus from said culture medium.

5. The recombinant Infectious Bursal Disease virus (IBDV) in ovo in a poultry ovum containing poultry maternal antibodies, according to claim 1, wherein the poultry ovum comprises a chicken egg.

6. The recombinant Infectious Bursal Disease virus (IBDV) in ovo in a poultry ovum containing poultry maternal antibodies, according to claim 1, wherein the poultry ovum comprises an embryonated chicken egg.

7. The recombinant Infectious Bursal Disease virus (IBDV) in ovo in a poultry ovum containing a poultry maternal antibodies, according to claim 1, wherein the poultry ovum comprises a 14-18 day old embryonated chicken egg.

8. The recombinant Infectious Bursal Disease virus (IBDV) in ovo in a poultry ovum containing poultry maternal antibodies, according to claim 6, wherein the recombinant IBDV is not neutralized by maternal antibodies present in said embryonated chicken egg, and the recombinant IBDV is non-lethal to an embryo of said embryonated chicken egg.

9. The recombinant Infectious Bursal Disease virus (IBDV) in ovo in a poultry ovum containing poultry maternal antibodies, according to claim 7, wherein the recombinant IBDV is not neutralized by maternal antibodies present in said embryonated chicken egg, and the recombinant IBDV is non-lethal to an embryo of said enbryonated chicken egg.

* * * * *

UNITED STATES PATENT AND TRADEMARK OFFICE
CERTIFICATE OF CORRECTION

PATENT NO. : 7,491,399 B2
APPLICATION NO. : 11/473735
DATED : February 17, 2009
INVENTOR(S) : Vikram Vakharia Page 1 of 1

It is certified that error appears in the above-identified patent and that said Letters Patent is hereby corrected as shown below:

Title Page 1 item 56, col. 1, line 5 References Cited, Other Publications, first column, second entry: "Does Not Cause Burdal Lesions" should be -- Does Not Cause Bursal Lesions --.

Title Page 1, col. 2, line 18 References Cited, Other Publications, second column, sixth entry: "Chicken Infectiuos Anaemia" should be -- Chicken Infectious Anaemia --.

Column 7, line 30: "1-200 ug" should be -- 1-200 $\mu$g --.

Column 14, line 38: "3544" should be -- 35-44 --.

Column 14, line 59: "MDA+chicken" should be -- MDA+ chicken --.

Column 33, line 23: "nucleotide sequence" should be -- nucleotide sequences --.

Column 33, line 33: "produce" should be -- produced --.

Signed and Sealed this

Twenty-first Day of April, 2009

JOHN DOLL
*Acting Director of the United States Patent and Trademark Office*